US009644017B2

(12) United States Patent
Habermann et al.

(10) Patent No.: US 9,644,017 B2
(45) Date of Patent: May 9, 2017

(54) INSULIN DERIVATIVES HAVING AN EXTREMELY DELAYED TIME-ACTION PROFILE

(75) Inventors: Paul Habermann, Frankfurt am Main (DE); Gerhard Seipke, Frankfurt am Main (DE); Roland Kurrle, Frankfurt am Main (DE); Gunter Muller, Frankfurt am Main (DE); Mark Sommerfeld, Frankfurt am Main (DE); Norbert Tennagels, Frankfurt am Main (DE); Georg Tschank, Frankfurt am Main (DE); Ulrich Werner, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 567 days.

(21) Appl. No.: 12/820,722

(22) Filed: Jun. 22, 2010

(65) Prior Publication Data

US 2011/0077197 A1    Mar. 31, 2011

Related U.S. Application Data

(63) Continuation of application No. PCT/EP2009/000017, filed on Jan. 6, 2009.

(60) Provisional application No. 61/044,659, filed on Apr. 14, 2008.

(30) Foreign Application Priority Data

Jan. 9, 2008 (DE) .................. 10 2008 003 568
May 24, 2008 (DE) .................. 10 2008 025 008

(51) Int. Cl.
A61K 38/00       (2006.01)
C07K 2/00        (2006.01)
C07K 14/62       (2006.01)

(52) U.S. Cl.
CPC ................... C07K 14/62 (2013.01)

(58) Field of Classification Search
None
See application file for complete search history.

(56) References Cited

U.S. PATENT DOCUMENTS

| | | | |
|---|---|---|---|
| 3,984,696 A | 10/1976 | Collica et al. | |
| 4,258,134 A | 3/1981 | Yoshida et al. | |
| 4,923,162 A | 5/1990 | Fleming et al. | |
| 5,006,718 A | 4/1991 | Lenhart | |
| 5,008,241 A * | 4/1991 | Markussen et al. | 514/6.2 |
| 5,358,708 A | 10/1994 | Patel | |
| 5,597,796 A * | 1/1997 | Brange | 514/6.2 |
| 5,656,722 A | 8/1997 | Doerschug | |
| 5,952,297 A | 9/1999 | DeFelippis et al. | |
| 5,981,964 A | 11/1999 | McAuley et al. | |
| 5,986,048 A | 11/1999 | Rubroder et al. | |
| 6,100,376 A * | 8/2000 | Dorschug | 530/303 |
| 6,174,856 B1 | 1/2001 | Langballe et al. | |
| 6,197,926 B1 | 3/2001 | Gaur et al. | |
| 6,444,641 B1 * | 9/2002 | Flora | 514/6.2 |
| 6,852,694 B2 | 2/2005 | Van Antwerp et al. | |
| 6,908,610 B1 | 6/2005 | Sato | |
| 7,205,277 B2 | 4/2007 | Boderke | |
| 7,476,652 B2 | 1/2009 | Brunner-Schwarz et al. | |
| 7,544,657 B2 * | 6/2009 | Ebbehoj et al. | 514/1.1 |
| 7,713,930 B2 | 5/2010 | Brunner-Schwarz et al. | |
| 8,048,854 B2 | 11/2011 | Habermann et al. | |
| 8,633,156 B2 | 1/2014 | Habermann et al. | |
| 2002/0132760 A1 | 9/2002 | Van Antwerp et al. | |
| 2004/0037893 A1 | 2/2004 | Hansen et al. | |
| 2004/0235710 A1 | 11/2004 | DeFelippis et al. | |
| 2005/0014679 A1 | 1/2005 | Beals et al. | |
| 2005/0171009 A1 | 8/2005 | Brunner-Schwarz et al. | |
| 2006/0014678 A1 | 1/2006 | Cowley et al. | |
| 2006/0019347 A1 | 1/2006 | Cho et al. | |
| 2006/0093576 A1 | 5/2006 | Chen et al. | |
| 2006/0194719 A1 | 8/2006 | Ebbehoj et al. | |
| 2007/0191271 A1 | 8/2007 | Mayhew et al. | |
| 2008/0064856 A1 | 3/2008 | Warne et al. | |

(Continued)

FOREIGN PATENT DOCUMENTS

| | | |
|---|---|---|
| CN | 1276731 | 12/2000 |
| CN | 1276731 A | 12/2000 |

(Continued)

OTHER PUBLICATIONS

Weiss et. al. (Activities of Monomeric Insulin Analogs at Position A8 Are Uncorrelated with Their Thermodynamic Stabilities, The Journal of Biological Chemistry, vol. 276, No. 43 pp. 40018-40024 , Oct. 26, 2001.*
Weiss et. al. Activities of Monomeric Insulin Analogs at Position A8 Are Uncorrelated with Their Thermodynamic Stabilities, The Journal of Biological Chemistry, vol. 276, No. 43 pp. 40018-40024 , Oct. 26, 2001.*
Markussen, J. et al., "Soluble, prolonged-acting insulin derivatives. III. Degree of Protraction, crystallizability and chemical stability of insulins substituted in positions A21, B13, B23, B27 and B30," Protein Engineering (1988), vol. 2, No. 2, pp. 157-166.
Kohn, Wayne D. et al., "pI-shifted insulin analogs with extended in vivo time action and favorable receptor selectivity," Peptides (2007), vol. 28, pp. 935-948.
Jekel, Peter A. et al., "Use of Endoproteinase Lys-C from Lysobacter enzymogenes in Protein Sequence Analysis," Analytical Biochemistry (1983), vol. 134, pp. 347-354.

(Continued)

Primary Examiner — Jeanette Lieb
(74) Attorney, Agent, or Firm — McDonnell Boehnen Hulbert & Berghoff LLP

(57) ABSTRACT

The invention relates to novel insulin analogs having a basal time-action profile, which are characterized by the following features: a) the B chain end consists of an amidated basic amino acid residue such as lysine or arginine amide; b) the N-terminal amino acid residue of the insulin A chain is a lysine or arginine radical; c) the amino acid position A8 is occupied by a histidine radical; d) the amino acid position A21 is occupied by a glycine radical; and e) one or more substitutions and/or additions of negatively charged amino acid residues are carried out in the positions A5, A15, A18, B-1, B0, B1, B2, B3 and B4.

37 Claims, 2 Drawing Sheets

(56) References Cited

U.S. PATENT DOCUMENTS

| | | |
|---|---|---|
| 2008/0248999 A1 | 10/2008 | Steiner |
| 2008/0260840 A1 | 10/2008 | Alessi et al. |
| 2009/0082255 A1 | 3/2009 | Brunner-Schwarz et al. |
| 2009/0142338 A1 | 6/2009 | Levetan |
| 2009/0214468 A1 | 8/2009 | Lin et al. |
| 2009/0304665 A1 | 12/2009 | Frost et al. |
| 2010/0279931 A1 | 11/2010 | Garibay et al. |
| 2011/0077197 A1 | 3/2011 | Habermann et al. |
| 2011/0173722 A1 | 7/2011 | Habermann et al. |
| 2012/0021978 A1 | 1/2012 | Werner et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0283179 A1 | 11/2012 | Brunner-Schwarz et al. |
| 2012/0295846 A1 | 11/2012 | Hagendorf et al. |
| 2014/0206611 A1 | 7/2014 | Becker et al. |
| 2014/0248365 A1 | 9/2014 | Rademacher et al. |

FOREIGN PATENT DOCUMENTS

| | | |
|---|---|---|
| DE | 196 37 230 | 3/1998 |
| EP | 0194864 | 9/1986 |
| EP | 0194864 A2 | 9/1986 |
| EP | 0214826 | 3/1987 |
| EP | 0368187 | 5/1990 |
| EP | 0368187 A2 | 5/1990 |
| EP | 0375437 | 6/1990 |
| EP | 0419504 | 4/1991 |
| EP | 0 668 282 A1 | 8/1995 |
| EP | 0668282 | 8/1995 |
| EP | 0678522 | 10/1995 |
| EP | 0 845 265 | 6/1998 |
| EP | 1 364 032 | 11/2003 |
| EP | 1 364 029 B1 | 12/2005 |
| EP | 1 222 207 B1 | 12/2007 |
| JP | 61-212598 | 9/1986 |
| JP | 63-99096 | 4/1988 |
| JP | 2-218696 | 8/1990 |
| JP | 3-504240 | 9/1991 |
| JP | 6-506444 | 7/1994 |
| JP | 2001-521004 | 11/2001 |
| JP | 2002-516880 | 6/2002 |
| JP | 2007-204498 | 8/2007 |
| JP | 2009-091363 | 4/2009 |
| TW | 157005 | 5/1991 |
| TW | 562806 | 11/2003 |
| WO | 88/06599 | 9/1988 |
| WO | WO 88/06599 | 9/1988 |
| WO | WO89/10937 A1 | 11/1989 |
| WO | WO90/11299 A1 | 10/1990 |
| WO | WO91/03550 A1 | 3/1991 |
| WO | 92/00321 | 1/1992 |
| WO | 92/12999 | 8/1992 |
| WO | WO 92/12999 | 8/1992 |
| WO | 96/34882 | 11/1996 |
| WO | WO 96/34882 | 11/1996 |
| WO | WO 97/48413 | 12/1997 |
| WO | WO98/08871 A1 | 3/1998 |
| WO | 99/21573 | 5/1999 |
| WO | WO 99/21573 | 5/1999 |
| WO | 99/62558 | 12/1999 |
| WO | WO01/04156 A1 | 1/2001 |
| WO | WO 01/24814 | 4/2001 |
| WO | WO01/25278 A1 | 4/2001 |
| WO | WO02/065985 A2 | 8/2002 |
| WO | WO02/068660 A1 | 9/2002 |
| WO | WO02/070722 A1 | 9/2002 |
| WO | WO 02/076495 | 10/2002 |
| WO | WO02/079250 A1 | 10/2002 |
| WO | WO 03/020201 | 3/2003 |
| WO | WO 03/053339 | 7/2003 |
| WO | WO03/053339 A2 | 7/2003 |
| WO | WO 03/101395 | 12/2003 |
| WO | WO 03/105888 | 12/2003 |
| WO | WO2004/005342 A1 | 1/2004 |
| WO | 2004/035623 | 4/2004 |
| WO | 2004/096854 | 11/2004 |
| WO | WO 2004/096854 | 11/2004 |
| WO | WO 2004/096854 A2 | 11/2004 |
| WO | 2004/107979 | 12/2004 |
| WO | WO 2005/046716 | 5/2005 |
| WO | 2006/029634 | 3/2006 |
| WO | WO 2006/029634 | 3/2006 |
| WO | WO 2006/029634 A2 | 3/2006 |
| WO | WO2006/058620 A2 | 6/2006 |
| WO | WO2007/031187 A1 | 3/2007 |
| WO | 2007/037607 | 4/2007 |
| WO | 2007/081821 | 7/2007 |
| WO | WO 2007/081821 A2 | 7/2007 |
| WO | WO2007/081824 A2 | 7/2007 |
| WO | 2007/095288 | 8/2007 |
| WO | WO 2007/109221 | 9/2007 |
| WO | 2008/006496 | 1/2008 |
| WO | 2008/034881 | 3/2008 |
| WO | 2008/124522 | 10/2008 |
| WO | 2008/133908 | 11/2008 |
| WO | WO 2008/145323 | 12/2008 |
| WO | WO 2009/004627 | 1/2009 |
| WO | 2009/048959 | 4/2009 |
| WO | 2009/056569 | 5/2009 |
| WO | 2009/087081 | 7/2009 |
| WO | WO 2009/087081 | 7/2009 |
| WO | WO 2009/087081 A2 | 7/2009 |
| WO | 2009/134380 | 11/2009 |
| WO | WO 2011/058083 | 5/2011 |
| WO | WO 2015/059302 | 4/2015 |

OTHER PUBLICATIONS

International Search Report dated Jun. 22, 2009 issued in PCT/EP2009/000017.

Kaarsholm N.C. et al., "Engineering Stability of the Insulin Monomer Fold with Application to Structure-Activity Relationships", Biochemistry 32(40):10773-10778 (Oct. 12, 1993).

Brange, "Design of Insulin Analogues for Meal-Related Therapy", J Diabetes Complications 7(2):106-12 (Apr.-Jun. 1993). Abstract Provided.

Brange et al., "Toward Understanding Insulin Fibrillation," Journal of Pharmaceutical Sciences, 86(5):517-25 (May 1997).

DrugBank, "Insulin glargine," available online at http://www.drugbank.ca/drugs/DB00047, 16 pages (accessed online Sep. 25, 2014).

Knudsen et al., "Potent Derivatives of Glucagon-like Peptide-1 with Pharmocokinetic Properties Suitable for Once Daily Administration," J. Med. Chem. 43:1664-69 (May 2000).

Markussen et al., "Soluble, prolonged-acting insulin derivatives. I. Degree of protraction and crystallizability of insulins substituted in the termini of the B-chain," Protein Eng. 1(3):205-13 (Jun. 1987).

Schubert-Zsilavecz & Wurglics, "Better Blood Glucose Levels in Diabetics-Insulin Glargin-A Long-Acting Insulin Analog", Pharmazie in Unserer Zeit pp. 125-130 (Jan. 2001). Translation Provided.

Tessari et al., "Insulin in Methionine and Homocysteine Kinetics in Healthy Humans: Plasma vs. Intracellular Models", Am J Physiol Endocrinol Metab 288(6):E1270-6 (Jun. 2005).

The Diabetes Control and Complications Trial Research Group, "The Effect of Intensive Treatment of Diabetes on the Development and Progression of Long-Term Complications in Insulin-Dependent Diabetes Mellitus", The New England Journal of Medicine, 329:977-86 (Sep. 1993).

Wan et al., "Enhancing the Activity of Insulin at the Receptor Interface: Crystal Structure and Photo-Cross-Linking of AS Analogues," Biochemistry, 43:16119-33 (Dec. 2004).

Yu et al., "Effect of Zinc Sulphate and Zinc Methionine on Growth, Plasma Growth Hormone Concentration, Growth Hormone Receptor and Insulin-Like Growth Factor-1 Gene Expression in Mice", Clin Exp Pharmacal Physiol 32(4):273-278 (Apr. 2005). Abstract Provided.

English translation of Taiwanese Search Report corresponding to ROC Patent Application No. 098100283; dated Oct. 7, 2013.

(56) References Cited

OTHER PUBLICATIONS

Non-Final Rejection issued in U.S. Appl. No. 13/382,772; mailed Apr. 10, 2013, pp. 1-48.
Non-Final Rejection issued in U.S. Appl. No. 13/382,772; mailed Nov. 21, 2013, pp. 1-42.
Final Rejection issued in U.S. Appl. No. 13/382,772; mailed Jun. 3, 2014, pp. 1-34.
Non-Final Rejection issued in U.S. Appl. No. 13/382,772; mailed Sep. 29, 2014, pp. 1-33.
Final Rejection issued in U.S. Appl. No. 13/382,772; mailed Sep. 10, 2015, pp. 1-36.
Non-Final Rejection issued in U.S. Appl. No. 12/280,727; mailed Jun. 27, 2012, pp. 1-8.
Final Rejection issued in U.S. Appl. No. 12/280,727; mailed Nov. 8, 2012, pp. 1-8.
European Office Action dated Feb. 19, 2014 received from related Application No. 09 701 358.5.
Markussen, J. et al., "Soluble, prolonged-acting insulin derivatives. I. Degree of protraction and crystallizability of insulins substituted in the termini of the B-chain" Protein Engineering (Jun. 1987) pp. 205-213, vol. 1, No. 3.
Markussen, J. et al., "Soluble, prolonged-acting insulin derivatives. II. Degree of protraction and crystallizability of 2 insulins substituted in positions A17, B8, B13, B27 and B30" Protein Engineering (Jun. 1987) pp. 215-223, vol. 1, No. 3. Abstract.
Markussen J. et al., "Soluble, Prolonged-Acting Insulin Derivatives. I. Degree of Protraction and Crystallizability of Insulins Substituted in the Termini of the B-Chain", Protein Engineering 1(3):205-213 (1987).
Markussen J. et al., "Soluble, Prolonged-Acting Insulin Derivatives. II. Degree of Protraction and Crystallizability of Insulins Substituted in Positions A17, B8, B13, B27 and B30", Protein Engineering 1(3):215-223 (1987).
English-language translation of Taiwanese Search Report dated Oct. 7, 2013 from related Application No. 098100283 and U.S. Appl. No. 12/820,727.
Japanese Notification of Reasons for Refusal dated Sep. 10, 2013 from related Application No. 2010-541744 and U.S. Appl. No. 12/820,727, together with an English-language translation.
English-language translation of Official Action dated Apr. 29, 2013 received from the Russian Patent Office from related Application No. 2010133233 and U.S. Appl. No. 12/820,727.
English-language translation of Official Action dated Dec. 14, 2012 received from the Russian Patent Office from related Application No. 2010133233 and U.S. Appl. No. 12/820,727.
U.S. Final Office Action dated Nov. 8, 2012 received from related U.S. Appl. No. 12/820,727.
U.S. non-final Office Action dated Jun. 27, 2012 received from related U.S. Appl. No. 12/820,727.
Final Rejection issued in U.S. Appl. No. 13/382,772; mailed Feb. 24, 2016, pp. 1-36.
Dunn et al., "Insulin Glargine: An Updated Review of its Use in the Management of Diabetes Mellitus" Drugs 63(16):1743-1778 (2003).
Brange & Langkjaer, "Insulin Structure and Stability" Chapter 11; Pharm Biotechnol 5:315-50 (1993).
Campbell et al., "Insulin Glargine," Clin. Therapeutics 23(12):1938-57 (2001).
Chi et al., "Excipients and their Effects on the Quality of Biologics" pp. 1-9, (May 2012).
Davis, How to Convert mg to mmol/L, available online at http://www.ehow.com/how_8498850_convert mg-mmoll.html (accessed on Nov. 11, 2015).
Fox et al., "Single amino acid substitutions on the surface of *Escherichia coli* maltose-binding protein can have a profound impact on the solubility of fusion proteins", Protein Science 10: 622-30 (2001).

Fransson et al., "Oxidation of Human Insulin-Like Growth Factor I in Formulation Studies: Kinetics of Methionine Oxidation in Aqueous Solution and in Solid State" Pharmaceutical Research 13(8):1252-57 (Aug. 1996).
Levine et al., "Oxidation of Methionine in Proteins: Roles in Antioxidant Defense and Cellular Regulation" IUBMB Life, 50:301-07 (Oct. 2000).
Non-Final Rejection issued in U.S. Appl. No. 13/382,442; mailed Mar. 31, 2016, pp. 1-29.
Final Rejection issued in U.S. Appl. No. 13/382,442; mailed Aug. 11, 2015, pp. 1-35.
Non-Final Rejection issued in U.S. Appl. No. 13/382,442; mailed Feb. 5, 2015, pp. 1-31.
Final Rejection issued in U.S. Appl. No. 13/382,442; mailed Jun. 13, 2014, pp. 1-29.
Non-Final Rejection issued in U.S. Appl. No. 13/382,442; mailed Dec. 19, 2013, pp. 1-29.
Final Rejection issued in U.S. Appl. No. 13/382,442; mailed Jul. 17, 2013, pp. 1-30.
Non-Final Rejection issued in U.S. Appl. No. 13/382,442; mailed Nov. 7, 2012, pp. 1-26.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
Search Report of the Intellectual Property Corporation of Malaysia for Malaysian Patent Application No. PI 2011006204; dated Sep. 15, 2015, pp. 1-3.
"Preferable." Merriam-Webster.com. Merriam-Webster, downloaded Sep. 7, 2015 at http://www.merriam-webster.com/dictionary/preferable.
Non-Final Rejection issued in U.S. Appl. No. 13/382,772; mailed Sep. 14, 2015, pp. 1-42.
U.S. Appl. No. 12/820,727, filed Jun. 22, 2010, Insulin Derivatives Having an Extremely Delayed Time-Action Profile, US20110173722, patented.
U.S. Appl. No. 13/382,772, filed May 29, 2012, Slow-Acting Insulin Preparations, US20120232002, pending.
U.S. Appl. No. 12/820,727, Jun. 22, 2010, Habermann et al.
U.S. Appl. No. 13/382,772, May 29, 2012, Schoettle et al.
U.S. Appl. No. 13/382,442, Mar. 21, 2012, Schoettle.
U.S. Appl. No. 13/509,542, Nov. 11, 2012, Hagendorf et al.
Bell et al., "Sequence of the human insulin gene." 284(5751):26-32 (Mar. 1980).
Giacometti et al., "In vitro activity of the histatin derivative P-113 against multidrug-resistant pathogens responsible or pneumonia in immunocompromised patients." 49(3):1249-52 (Mar. 2005).
Osterbye et al., "Sulfatide promotes the folding of proinsulin, preserves insulin crystals, and mediates its monomerization." Glycobiology 11(6):473-79 (Jun. 2001).
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (Jan. 2011).
RPMI-1640 Media Formulation, Sigma Aldrich, accessed on Jul. 10, 2016, pp. 1-5.
Rothstein et al., "Anticandida activity is retained in P-113, a 12-amino-acid fragment of histatin 5." Antimicrob Agents Chemother. 45(5):1367-73 (May 2001).
Tews et al., "Enhanced protection against cytokine—and fatty acid-induced apoptosis in pancreatic beta cells by combined treatment with glucagon-like peptide-1 receptor agonists and insulin analogues." Horm Metab Res. 40 (3)172-80 (Mar. 2008).
Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).
International Search Report by the ISA for International Application No. PCT/EP2009/000018; mailed Jun. 30, 2009, pp. 1-8.

* cited by examiner

INSULIN DERIVATIVES HAVING AN EXTREMELY DELAYED TIME-ACTION PROFILE

CROSS REFERENCE TO RELATED APPLICATIONS

This application is a continuation of International application No. PCT/EP2009/000,017, filed Jan. 6, 2009, which is incorporated herein by reference in its entirety; which claims the benefit of U.S. Provisional Application No. 61/044,659, filed Apr. 14, 2008 and the benefit of priority of German Patent Application No. 10 2008 003 568.8, filed Jan. 9, 2008 and the benefit of priority of German Patent Application No. 10 2008 025 008.2, filed May 24, 2008.

BACKGROUND OF THE INVENTION

Field of the Invention

The invention relates to novel insulin analogues with basal time/action profile, their preparation and use.

Description of the Art

The incidence of diabetes has increased in recent years to an almost epidemic extent. The disorder may result in a serious shortening of life expectancy. People with diabetes must frequently supply their body with insulin from outside. It is sensible to optimize the treatment with insulin. Different insulins with specific pharmacological properties are now available. In practice, the different insulins are differentiated according to their duration of action into short-acting insulins, fast-acting insulins, long-acting insulins and mixed insulins. Designations used synonymously for long-acting insulins are slow insulins, depot insulin or else basal insulin. The active ingredients in many of these insulin products are so-called insulin analogues which have been derived from human insulin by substitution, deletion and/or addition of one or more amino acids. The terms "insulin analogues" and "insulins" are used synonymously herein.

The policy of intensified insulin therapy attempts to diminish the health risk by aiming at a stable control of the blood glucose level by early administration of basal insulins. One example of a current basal insulin is the medicament Lantus® (active ingredient: insulin glargine=Gly (A21), Arg (B31), Arg (B32) human insulin). The general aim of developing novel, improved basal insulins is to minimize the number of hypoglycemic events. An ideal basal insulin in this connection is one acting reliably for at least 24 hours in each patient. The insulin effect ideally has a delayed onset and a time/action profile which is as shallow as possible, so that the risk of brief hypoglycemia is distinctly minimized and administration is even possible without previous intake of foodstuffs. There is a good supply of basal insulin when the insulin effect persists at the same level for as long as possible, i.e. the body is supplied with a constant amount of insulin. The risk of hypoglycemic events is thus low and a patient- and a day-specific variability is minimized. The pharmacokinetic profile of an ideal basal insulin should thus be characterized by a delayed onset of action and by a delayed, i.e. long-lasting and uniform, action.

However—despite the therapeutic advantages already achieved—none of the slow insulins described to date shows the pharmacokinetic properties of an ideal basal insulin. Desirable insulins have such a shallow and long-lasting time/action profile that the risk of hypoglycemic events and of the day-dependent variations in the patient is further minimized and the duration of action is further delayed, so that it is no longer necessary in some circumstances to administer insulin daily. This would make simplified treatment of diabetics possible, especially of elderly diabetics and those in need of care, who are no longer able to inject insulin themselves, and would thus also be of great economic benefit. Such basal insulins would additionally be beneficial in the early phase of type 2 diabetes. Clinicians report that the injection phobia present in many people deters them from starting insulin therapy in good time. As a consequence, the control of blood glucose is poor, leading to the late sequelae of diabetes. A basal insulin which reduces the number of insulin doses given by injection might have the effect of making insulin therapy more acceptable to patients.

Kohn et al. (Peptides 28 (2007) 935-948) describe how it is possible to optimize the pharmacodynamics of insulin by preparing insulin analogues whose isoelectric point (pI) is shifted, by addition of lysine or arginine at the B chain end or at the N terminus of the A and B chain, in the direction of the alkaline range compared with the isoelectric point of human insulin (pI=5.6), so that the solubility under physiological conditions is reduced and a prolonged time/action profile results. Compound 18 from Kohn et al. (Arg (A0), Gly (A21), Arg (B31), Arg (B32) human insulin (experimentally determined pI=7.3; calculated pI=7.58) is described in this connection as the best compound in the context of the idea. Kohn et al. therefore regard the main aim in designing novel insulin analogues as being the addition of positively charged amino acids to the amino acid sequence of human insulin for the purpose of increasing the isoelectric point from pI=5.6 into the neutral range.

This aim in the design of novel insulin analogues is the opposite of substitution of neutral amino acids in human insulin by acidic amino acids and/or addition of acidic amino acids, because such a substitution and/or additions at least partly abolishes the effect of introducing positively charged amino acids. However, it has now surprisingly been found that the described desirable basal time/action profile is obtained with insulin analogues which are characterized by the features that

- the B chain end consists of an amidated basic amino acid residue such as lysine or argininamide, and
- the N-terminal amino acid residue of the insulin A chain is a lysine or arginine residue, and
- the A8 amino acid position is occupied by a histidine residue, and
- the A21 amino acid position is occupied by a glycine residue, i.e. in the amidated basic amino acid residue at the B chain end the carboxyl group of the terminal amino acid is present in its amidated form, and
- there have been two substitutions of neutral amino acids by acidic amino acids, two additions of negatively charged amino acid residues or one such substitution and one such addition respectively in the A5, A15, A18, B-1, B0, B1, B2, B3 and B4 positions.

Whereas the first three features mentioned tend, through introduction of positive charges or elimination of negative charges, to contribute to increasing the pI of a corresponding insulin analogue, the last-mentioned substitutions and/or additions of negatively charged amino acid residues have the opposite effect and contribute to reducing the pI. Surprisingly, precisely the insulin analogues described have the desired advantageous time/action profiles. The pI values of these compounds are lower than that of compound 18 from Kohn et al. (Arg (A0), Gly (A21), Arg (B31), Arg (B32) human insulin), but nevertheless moreover show a delayed onset of action and a longer duration of action, i.e. an extremely shallow and long-lasting, uniform action profile.

The risk of hypoglycemic events is thus distinctly minimized. The delay is so marked that it is surprisingly possible to detect the effect even in model experiments on rats, although the delayed action of insulin glargine cannot by contrast be unambiguously observed in rats. FIG. 1 shows the hypoglycemic effect of the compound YKL205 of the invention compared with that of insulin glargine. Similar results are obtained in dogs (see FIG. 2). Thus, novel basal insulins which need to be administered distinctly less frequently have been provided. Besides these pharmacokinetic advantages described, the analogues of the invention show distinctly better properties compared with insulin glargine in pharmacological respects such as, for example, receptor specificity and in vitro mitogenicity. The claimed insulins also show advantages in physicochemical respects.

SUMMARY OF THE INVENTION

The invention thus relates to an insulin analogue of the formula I

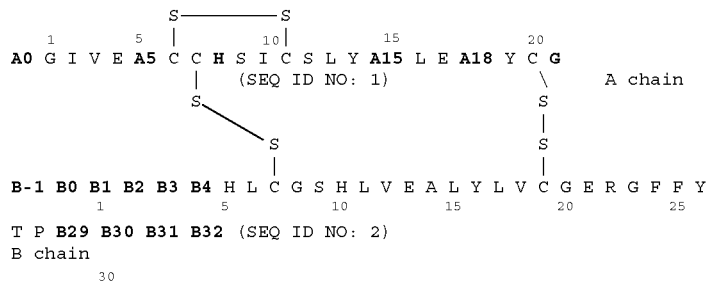

where
A0 corresponds to Lys or Arg;
A5 corresponds to Asp, Gln or Glu;
A15 corresponds to Asp, Glu or Gln;
A18 corresponds to Asp, Glu or Asn;
B-1 corresponds to Asp, Glu or an amino group;
B0 corresponds to Asp, Glu or a chemical bond;
B1 corresponds to Asp, Glu or Phe;
B2 corresponds to Asp, Glu or Val;
B3 corresponds to Asp, Glu or Asn;
B4 corresponds to Asp, Glu or Gln;
B29 corresponds to Lys or a chemical bond;
B30 corresponds to Thr or a chemical bond;
B31 corresponds to Arg, Lys or a chemical bond;
B32 corresponds to Arg-amide, Lys-amide or an amino group,
where two amino acid residues of the group comprising A5, A15, A18, B-1, B0, B1, B2, B3 and B4 correspond simultaneously and independently of one another to Asp or Glu.

DETAILED DESCRIPTION OF THE INVENTION

Figure 1:
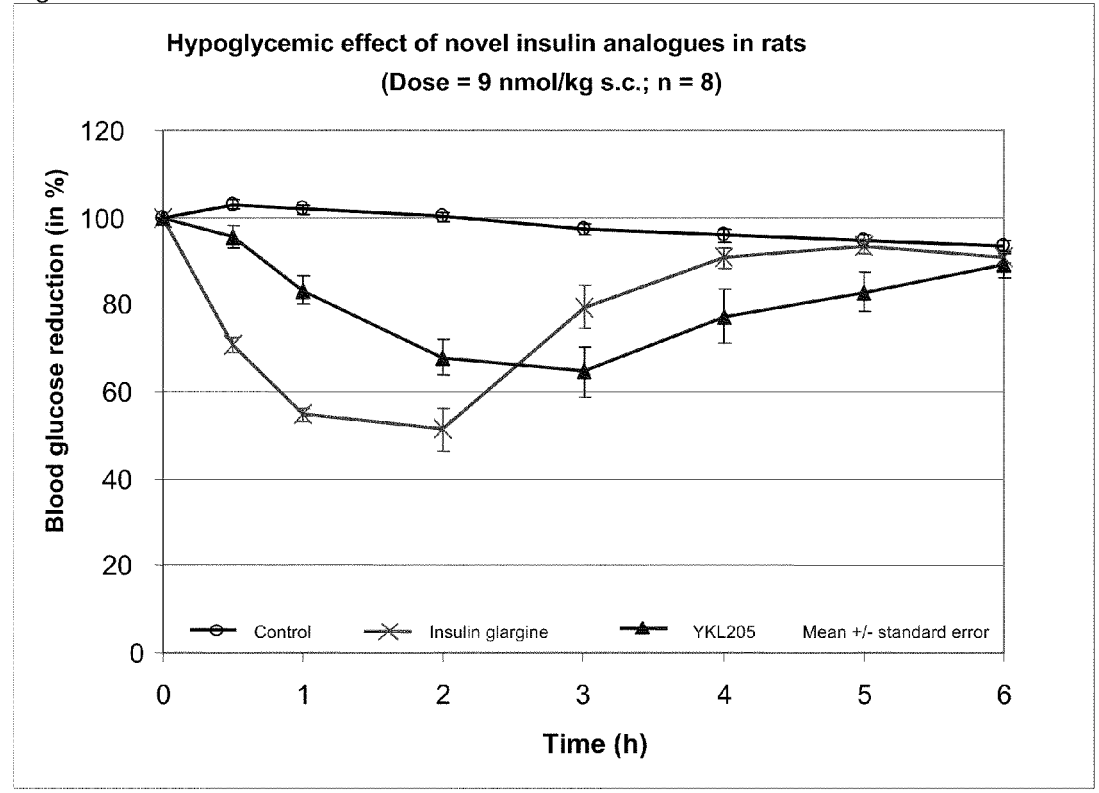
FIG. 1 shows hypoglycemic effect of novel insulin analogues in rats (Dose=9 nmol/kg s.c.; n=8).

The invention relates in particular to insulin analogues as detailed above in which independently of one another A0 corresponds to Arg, or where A5 corresponds to Glu, or where A15 corresponds to Glu, or where A18 corresponds to Asp, or where B-1 corresponds to an amino group, or where B0 corresponds to Glu, or where B1 corresponds to Asp, or where B2 corresponds to Val, or where B3 corresponds to Asp, or where B4 corresponds to Glu, or where B29 corresponds to Lys, or where B30 corresponds to Thr, or where B31 corresponds to Arg or Lys.

The invention particularly preferably relates to an insulin analogue selected from the group comprising:

Arg (A0), His (A8), Glu (A5), Asp (A18), Gly (A21), Arg (B31), Arg (B32)—NH$_2$ human insulin, Arg (A0), His (A8), Glu (A5), Asp (A18), Gly (A21), Arg (B31), Lys (B32)—NH$_2$ human insulin, Arg (A0), His (A8), Glu (A15), Asp (A18), Gly (A21), Arg (B31), Arg (B32)—NH$_2$ human insulin, Arg (A0), His (A8), Glu (A15), Asp (A18), Gly (A21), Arg (B31), Lys (B32)—NH$_2$ human insulin, Arg (A0), His (A8), Glu(A5), Glu (A15), Gly (A21), Arg (B31), Arg (B32)—NH$_2$ human insulin, Arg (A0), His (A8), Glu (A5), Glu (A15), Gly (A21), Arg (B31), Lys (B32)—NH$_2$ human insulin, Arg (A0), His (A8), Glu (A5), Gly (A21), Asp (B3), Arg (B31), Arg (B32)—NH$_2$ human insulin, Arg (A0), His (A8), Glu (A5), Gly (A21), Asp (B3), Arg (B31), Lys (B32)—NH$_2$ human insulin, Arg (A0), His (A8), Glu (A15), Gly (A21), Asp (B3), Arg (B31), Arg (B32)—NH$_2$ human insulin, Arg (A0), His (A8), Glu (A15), Gly (A21), Asp (B3), Arg (B31), Lys (B32)—NH$_2$ human insulin, Arg (A0), His (A8), Asp (A18), Gly (A21), Asp (B3), Arg (B31), Arg (B32)—NH$_2$ human insulin, Arg (A0), His (A8), Asp (A18), Gly (A21), Asp (B3), Arg (B31), Lys (B32)—NH$_2$ human insulin, Arg (A0), His (A8), Gly (A21), Asp (B3), Glu (B4), Arg (B31), Arg (B32)—NH$_2$ human insulin, Arg (A0), His (A8), Gly (A21), Asp (B3), Glu (B4), Arg (B31), Lys (B32)—NH$_2$ human insulin, Arg (A0), His (A8), Glu (A5), Gly (A21), Glu (B4), Arg (B31), Arg (B32)—NH$_2$ human insulin, Arg (A0), His (A8), Glu (A5), Gly (A21), Glu (B4), Arg (B31), Lys (B32)—NH$_2$ human insulin, Arg (A0), His (A8), Glu (A15), Gly (A21), Glu (B4), Arg (B31), Arg (B32)—NH$_2$ human insulin, Arg (A0), His (A8), Glu (A15), Gly (A21), Glu (B4), Arg (B31), Lys (B32)—NH$_2$ human insulin,
Arg (A0), His (A8), Asp (A18), Gly (A21), Glu (B4), Arg (B31), Arg (B32)—NH$_2$ human insulin,
Arg (A0), His (A8), Asp (A18), Gly (A21), Glu (B4), Arg (B31), Lys (B32)—NH$_2$ human insulin,
Arg (A0), His (A8), Glu (A5), Gly (A21), Glu (B0), Arg (B31), Arg (B32)—NH$_2$ human insulin,
Arg (A0), His (A8), Glu (A5), Gly (A21), Glu (B0), Arg (B31), Lys (B32)—NH$_2$ human insulin,
Arg (A0), His (A8), Glu (A15), Gly (A21), Glu (B0), Arg (B31), Arg (B32)—NH$_2$ human insulin,
Arg (A0), His (A8), Glu (A15), Gly (A21), Glu (B0), Arg (B31), Lys (B32)—NH$_2$ human insulin,
Arg (A0), His (A8), Asp (A18), Gly (A21), Glu (B0), Arg (B31), Arg (B32)—NH$_2$ human insulin,
Arg (A0), His (A8), Asp (A18), Gly (A21), Glu (B0), Arg (B31), Lys (B32)—NH$_2$ human insulin,
Arg (A0), His (A8), Glu (A5), Gly (A21), Asp (B1), Arg (B31), Arg (B32)—NH$_2$ human insulin,
Arg (A0), His (A8), Glu (A5), Gly (A21), Asp (B1), Arg (B31), Lys (B32)—NH$_2$ human insulin,
Arg (A0), His (A8), Glu (A15), Gly (A21), Asp (B1), Arg (B31), Arg (B32)—NH$_2$ human insulin,
Arg (A0), His (A8), Glu (A15), Gly (A21), Asp (B1), Arg (B31), Lys (B32)—NH$_2$ human insulin,
Arg (A0), His (A8), Asp (A18), Gly (A21), Asp (B1), Arg (B31), Arg (B32)—NH$_2$ human insulin,
Arg (A0), His (A8), Asp (A18), Gly (A21), Asp (B1), Arg (B31), Lys (B32)—NH$_2$ human insulin,
Arg (A0), His (A8), Gly (A21), Glu (B0), Asp (B1), Arg (B31), Arg (B32)—NH$_2$ human insulin,
Arg (A0), His (A8), Gly (A21), Glu (B0), Asp (B1), Arg (B31), Lys (B32)—NH$_2$ human insulin,
Arg (A0), His (A8), Asp (A18), Gly (A21), Asp (B3), Arg (B30), Arg (B31)—NH$_2$ human insulin,
Arg (A0), His (A8), Asp (A18), Gly (A21), Asp (B3), Arg (B30), Lys (B31)—NH$_2$ human insulin.

Specification of the term "human insulin" in the designations of the insulin analogues mentioned makes reference to the amino acid sequences of the A chain and B chain of human insulin, and all deviations (additions, substitutions, deletions) therefrom are indicated in a given designation of an insulin analogue.

The invention further relates to a process for preparing an insulin analogue as mentioned above, in particular where a precursor of the insulin analogue is prepared recombinantly, the precursor is processed enzymatically to two-chain insulin, and a coupling with argininamide is carried out in the presence of an enzyme having trypsin activity, and the insulin analogue is isolated.

The invention further relates to a use of an insulin analogue as described above for the manufacture of a medicament for the treatment of diabetes, in particular of diabetes of type I or type II. The invention likewise relates to a use of an insulin analogue as described above for the manufacture of a medicament for assisting beta cell regeneration.

The invention further relates to a pharmaceutical comprising an insulin analogue as described above and/or physiologically acceptable salts thereof.

The invention further relates to a formulation of the insulin analogue as described above, where the formulation is in aqueous form comprising the dissolved insulin analogue.

The invention further relates to a formulation of the insulin analogue as described above, where the formulation is in the form of powder.

The invention further relates to a formulation as described above, where the insulin analogue as described above is present in crystalline and/or amorphous form.

The invention further relates to a formulation of the insulin analogue as described above, where the formulation is in the form of a suspension.

The invention further relates to a formulation of the insulin analogue as described above, where the formulation additionally comprises a chemical chaperone.

The invention further relates to a DNA coding for a precursor of an insulin analogue as described above, or for the A chain or B chain of an insulin analogue as described above.

The invention further relates to a vector comprising a DNA as described above.

The invention further relates to a host organism comprising a DNA as described above or a vector as described above.

The invention further relates to a preproinsulin analogue, wherein the C peptide carries the amino acid residue arginine at its N terminus and two arginine residues or one arginine residue and one lysine residue on its C terminus, and in the latter case the lysine residue forms the actual C terminus.

The invention further relates to a formulation as described above which additionally comprises also a glucagon-like peptide-1 (GLP1) or an analogue or derivative thereof, or exendin-3 or -4 or an analogue or derivative thereof, preferably exendin-4.

The invention further relates to a formulation as described above in which an analogue of exendin-4 is selected from a group comprising
H-desPro$^{36}$-exendin-4-Lys$_6$-NH$_2$,
H-des(Pro$^{36,37}$)-exendin-4-Lys$_4$-NH$_2$ and
H-des(Pro$^{36,37}$)-exendin-4-Lys$_5$-NH$_2$,
or a pharmacologically tolerable salt thereof.

The invention further relates to a formulation as described above in which an analogue of exendin-4 is selected from a group comprising
desPro$^{36}$ [Asp$^{28}$]exendin-4 (1-39),
desPro$^{36}$ [IsoAsp$^{28}$]exendin-4 (1-39),
desPro$^{36}$ [Met(O)$^{14}$, Asp$^{28}$]exendin-4 (1-39),
desPro$^{36}$ [Met(O)$^{14}$, IsoAsp$^{28}$]exendin-4 (1-39),
desPro$^{36}$ [Trp(O$_2$)$^{25}$, Asp$^{28}$]exendin-2 (1-39),
desPro$^{36}$ [Trp(O$_2$)$^{25}$, IsoAsp$^{28}$]exendin-2 (1-39),
desPro$^{36}$ [Met(O)$^{14}$Trp(O$_2$)$^{25}$, Asp$^{28}$]exendin-4 (1-39) and
desPro$^{36}$ [Met(O)$^{14}$Trp(O$_2$)$^{25}$, IsoAsp$^{28}$]exendin-4 (1-39),
or a pharmacologically tolerable salt thereof.

The invention further relates to a formulation as described in the preceding paragraph, in which the peptide -Lys$_6$-NH$_2$ is attached to the C termini of the analogues of exendin-4.

The invention further relates to a formulation as described above in which an analogue of exendin-4 is selected from a group comprising
H-(Lys)$_6$-des Pro$^{36}$ [Asp$^{28}$]exendin-4(1-39)-Lys$_6$-NH$_2$
des Asp$^{28}$Pro$^{36}$, Pro$^{37}$, Pro$_{38}$ exendin-4(1-39)—NH$_2$,
H-(Lys)$_6$-des Pro$^{36}$, Pro$^{37}$, Pro$^{38}$ [Asp$^{28}$]exendin-4(1-39)—NH$_2$,
H-Asn-(Glu)$_5$ des Pro$^{36}$, Pro$^{37}$, Pro$^{38}$ [Asp$^{28}$]exendin-4(1-39)—NH$_2$,
des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$, Pro$^{37}$, Pro$^{38}$ [Asp$^{28}$]exendin-4(1-39)-(Lys)$_6$-NH$_2$, H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$ [Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Trp(O$_2$)$^{25}$]exendin-4(1-39)—NH$_2$,
H-(Lys)$_6$-des Pro$^{36}$, Pro$^{37}$, Pro$^{38}$ [Trp(O$_2$)$^{25}$, Asp$^{28}$]exendin-4(1-39)—NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)—NH$_2$,
des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)—NH$_2$,
H-(Lys)$_6$-des Pro$^{36}$, Pro$^{37}$, Pro$^{38}$ [Met(O)$^{14}$, Asp$^{28}$]exendin-4(1-39)—NH$_2$,
H-Asn-(Glu)$_5$-des Pro$^{36}$, Pro$^{37}$, Pro$^{38}$ [Met(O)$^{14}$, Asp$^{28}$]exendin-4(1-39)—NH$_2$,
des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$]exendin-4(1-39)-Lys$_6$-NH$_2$,
H-Asn-(Glu)$_5$ des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$ [Met(O)$^{14}$, Trp(O$_2$)$^{25}$, Asp$^{28}$]exendin-4(1-39)-Lys$_6$-NH$_2$,
des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36}$, Pro$^{37}$, Pro$^{38}$ [Met(O)$^{14}$, TrP(O$_2$)$^{25}$, Asp$^{28}$]exendin-4(1-39)—NH$_2$,
H-Asn-(Glu)$_5$-des Pro$^{36}$, Pro$^{37}$, Pro$^{38}$ [Met(O)$^{14}$, Asp$^{28}$]exendin-4(1-39)—NH$_2$,
des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$]exendin-4(1-39)-(Lys)-NH$_2$,
or a pharmacologically tolerable salt thereof.

The invention further relates to a formulation as described above which additionally comprises Arg$^{34}$, Lys$^{26}$ (N$^\epsilon$(γ-glutamyl(N$^\alpha$-hexadecanoyl))) GLP-1 (7-37) [liraglutide] or a pharmacologically tolerable salt thereof.

It is clear to a skilled worker in this connection that the insulins of the invention may be item of a pharmaceutical formulation which has an advantageous effect after administration. Aqueous solutions are the starting point in this connection. Further components must accordingly be miscible. The risk of viral animal contamination is minimized in that the preparation ought not to comprise any components derived from animal sources. It is further advantageous to prevent microbial contamination by adding preservatives. It is possible by adding isotonic agents to compensate for a possible negative effect of the formulation on the physiology of the tissue cells at the administration site. The addition of protamine may have a stabilizing effect, so that substantially salt-free insulin preparation can be obtained by adding protamine to the formulation. Addition of a phenolic component may lead to stabilization of the structure of the insulin analogue used and thus additionally bring about inter alia the delaying effect on the onset of action. It is also possible to add to the formulation substances which stabilize the spatial structure of the slow insulins of the invention and lead to better thermal stability. Such chemical chaperones may be for example short synthetic peptides, which may also comprise amino acid analogues or include for example peptide sequences derived from the C peptide of insulin.

The insulins of the invention can be incorporated into nanoparticles for developing depot forms. Also conceivable are so-called slow release formulations in which the slow insulin of the invention is present reversibly bound to a polymer carrier.

The insulins of the invention can be administered in parallel with fast-acting insulin such as insulin glulisine (APIDRA®), NovoRapid®, insulin lispro (HUMALOG®) or insulin derivatives undergoing development or formulations with an appropriate time/action profile or inhalable insulin or nasally or orally administered insulins which are undergoing development. It will be clear to a skilled worker in this connection that appropriately formulated mixtures of fast-acting and slow insulin of the invention can also be used for this purpose. The insulin analogues of the invention can further be used in pharmaceutical preparations which comprise peptides which are described by an activity comparable to GLP-1 (glucagon like Peptide-1) or exendin-4 or exendin-3. GLP-1 (7-37), exenatide (BYETTA®) or peptides whose preparation is described in the patent applications WO 2006/058620, WO 2001/04156, WO 2004/005342 and WO 98/08871 represent examples of such peptides. Formulations particularly advantageous in this connection are those comprising a depot formulation of these peptides. Types of therapy advantageous especially in the initial phase of type II diabetes are those which provide in parallel with the administration of the pharmaceuticals of the invention, which increase the effect of insulin, such as, for example, metformin. Combination therapies with dipeptidyl peptidase-4 inhibitors which increase the level of incretins are, like combinations with sulfonylureas which increase insulin secretion in the pancreas, likewise possible. The slow insulins of the invention can be employed particularly advantageously when regeneration of pancreatic beta cells from appropriate stem cells is initiated by administration of differentiation factors. All these applications are mentioned by way of example for the therapy of diabetes, and the invention likewise relates thereto. The invention thus further relates to the use of the insulins of the invention in combination with other active ingredients for the treatment of diabetes, especially diabetes of type I or type II diabetes.

The invention further relates to a pharmaceutical which comprises an insulin analogue of the invention which represents in particular an aqueous formulation or a powder.

The pharmaceutical is a pharmaceutical preparation which is preferably a solution or suspension for injection purposes; it is characterized by a content of at least one insulin analogue of the invention, and/or at least one of the physiologically tolerated salts thereof in dissolved, amorphous and/or crystalline—preferably in dissolved—form.

The preparation preferably has a pH of between about 2.5 and 8.5, in particular between 4.0 and 8.5, preferably comprises a suitable tonicity agent, a suitable preservative and, where appropriate, a suitable buffer, and preferably also a particular zinc ion concentration, in sterile aqueous solution. The totality of the preparation ingredients apart from the active ingredient forms the preparation carrier. Suitable tonicity agents are for example glycerol, glucose, mannitol, NaCl, calcium or magnesium compounds such as CaCl$_2$ etc. The solubility of the insulins of the invention or the physiologically tolerated salts thereof at weakly acidic pH values is influenced by the choice of the tonicity agent and/or preservative.

Examples of suitable preservatives are phenol, m-cresol, benzyl alcohol and/or p-hydroxybenzoic esters.

Buffer substances which can be used in particular for adjusting a pH between about 4.0 and 8.5 are for example sodium acetate, sodium citrate, sodium phosphate etc. Otherwise, physiologically acceptable dilute acids (typically HCl) or alkalis (typically NaOH) are also suitable for adjusting the pH.

If the preparation has a zinc content, preference is given to one of from 1 to 2 mg/ml, in particular from 1 μg/ml to 200 μg zinc/ml.

The action profile of the insulin analogues of the invention can surprisingly be influenced satisfactorily by adding Zn. This allows preparations which differ in relation to the total duration of action, the speed of onset of action and the profile of the effect curve and thus allow individual stabilization of the patient. Another possibility arises through the use of a "two-chamber insulin device" which allows a formulation with a rapid onset of action and/or slow gradual onset of action to be administered depending on the life situation.

For the purpose of varying the active ingredient profile of the preparation of the invention it is also possible to admix unmodified insulin, preferably bovine, porcine or human insulin, especially human insulin, or insulin analogues and derivatives thereof. It is likewise possible to admix one or more exendin-4 derivatives or peptides which are characterized by an activity comparable to GLP-1 (glucagon like peptide-1) or correspond directly to GLP-1. The invention likewise relates to such pharmaceuticals (preparations).

Preferred active ingredient concentrations are those corresponding to about 1-1500, more preferably about 5-1000 and in particular about 40-400 international units/ml.

The insulin analogues of the invention are initially prepared biotechnologically as precursor which does not yet include the amide. The skilled worker is familiar with a large number of possibilities for preparing insulins. Host cell systems used in this connection are bacteria, yeasts and plants or plant cells for cultivation by fermentation. If cost considerations permit, expression systems which use animal cells as host system are also conceivable. However, the precondition therefor is reliable freedom from animal viruses. It is thus clear that the expression systems described by way of example represent only a small segment of the host/vector systems developed for the recombinant preparation of proteins. For example, biotechnological processes based on yeast or plant systems such as mosses, algae or higher plants such as tobacco, pea, safflower, barley, corn or oilseed rape are not described in the application. Nevertheless, the invention likewise includes host/vector systems and coding DNA sequences which allow the target peptides to be prepared in appropriate biotechnological expression systems. Host organisms can thus be selected in particular from the plant kingdom from organisms of the first division Schizophyta comprising Schizomycetes, bacteria or blue algae, organisms of the $2^{nd}$ division Phycophyta class V Chlorophyceae, organisms of the $2^{nd}$ division Phycophyta class VII Rhodophyceae, organisms of the $3^{rd}$ division Mycophyta, organisms of the $5^{th}$ division Bryophyta and organisms of the $7^{th}$ division Spermatophyta.

European patent application EP-A 1 222 207 describes a plasmid pINT358d which codes for a preproinsulin which includes a modified C peptide. It is now possible with the aid of the polymerase chain reaction (PCR) to modify the proinsulin-encoding sequence specifically so that it is possible to express preproinsulins which can serve as precursors of the insulins of the invention. Corresponding fusion proteins need not necessarily be prepared intracellularly. It is clear to the skilled worker that such proteins can also be prepared by bacterial expression with subsequent secretion into the periplasm and/or into the culture supernatant. European patent application EP-A 1 364 029 describes this by way of example. The invention likewise relates to the proinsulin precursors which lead to the analogues of the invention.

The proinsulins prepared in this way can in principle be converted into an insulin analogue precursor which includes lysine or arginine in position A0 and carries lysine or arginine at the C-terminal end of the B chain.

If the proinsulins of the invention are in the form of inclusion bodies or soluble form after intracellular expression in bacteria, these precursors must be folded by in vitro folding into the correct conformation before the processing and biochemical modification can be undertaken. In this connection, the described fusion protein allows direct folding after denaturation by means of urea or guanidinium hydrochloride, and the invention likewise relates to folding intermediates.

Biochemical methods are used to concentrate the individual intermediates, especially separation processes whose underlying principles are published and in fact the subject of textbooks. It is clear to the skilled worker that such principles can consequently be combined and thus may lead to processes which have not previously been published in their sequence. The invention thus likewise relates to processes which lead to purification of the analogues of the invention.

The invention further relates to a process for preparing the insulin analogues of the invention, where a precursor of the insulin analogue is prepared recombinantly and converted enzymatically into a two-chain insulin precursor which carries arginine or lysine N-terminally in relation to amino acid 1 of the A chain, and has at the C-terminal end of the B chain a lysine or arginine residue which is converted with argininamide or lysinamide in the presence of an enzyme having trypsin activity into the amide and thus into the slow insulin of the invention, and is prepared with high purity by a biochemical purification process.

Proteins which differ through substitution of at least one naturally occurring amino acid residue by other amino acid residues and/or addition and/or deletion of at least one amino acid residue from the corresponding, otherwise identical naturally occurring protein are referred to as "analogues" of proteins. It is also possible in this connection for the added and/or replaced amino acid residues to be ones which do not occur naturally.

Proteins which are obtained by chemical modification of certain amino acid residues of initial proteins are referred to as "derivatives" of proteins. The chemical modification may consist for example of addition of one or more particular chemical groups to one or more amino acids.

Figure 2:
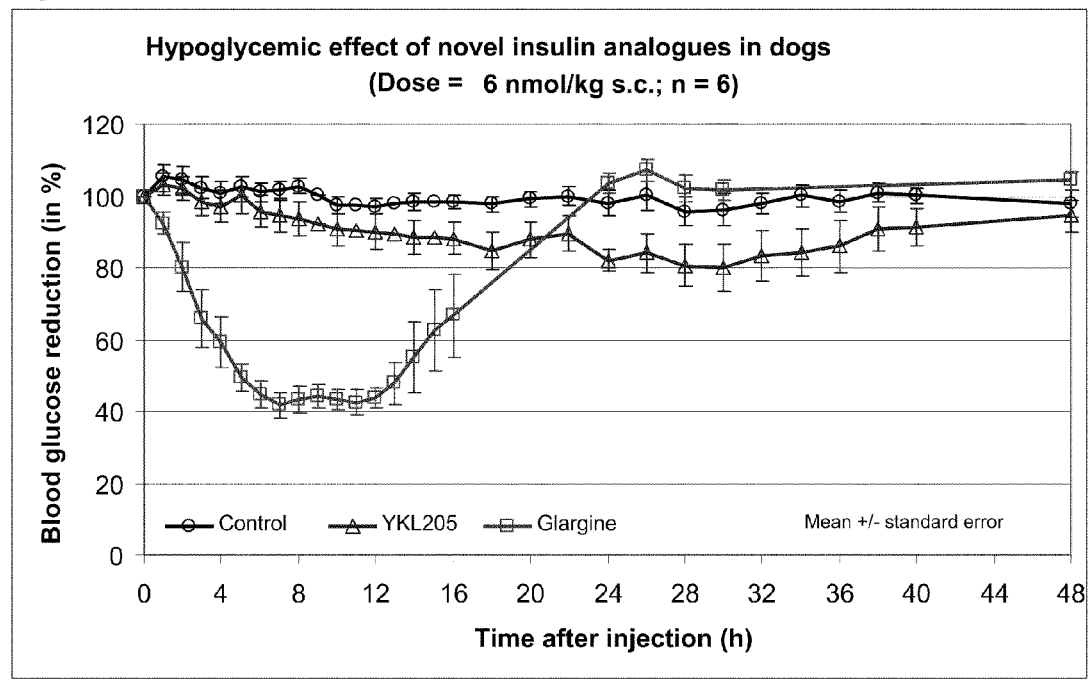
FIG. 2 shows hypoglycemic effect of novel insulin analogues in dogs (Dose=6 nmol/kg s.c.; n=6).
Figure 3:
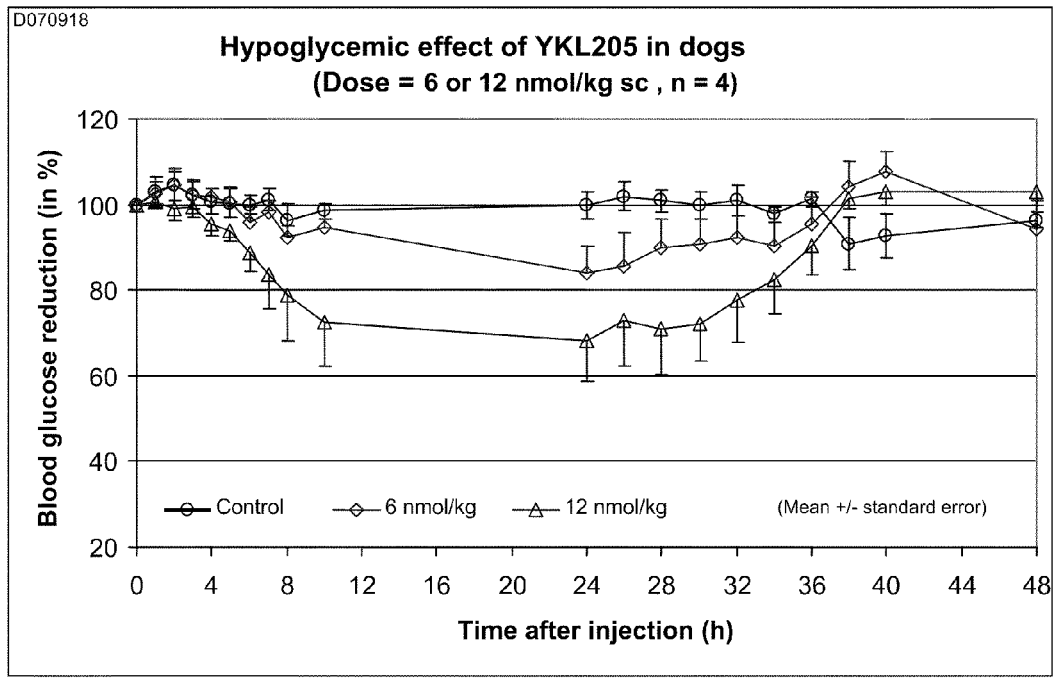
FIG. 3 shows hypoglycemic effect of YKL205 in dogs (Dose=6 or 12 nmol/kg s.c., n=4).

Key To Figures:
FIG. 1: Blood glucose-lowering effect of novel insulin analogues in rats
FIG. 2: Blood glucose-lowering effect of novel insulin analogues in dogs
FIG. 3: Blood glucose-lowering effect of YKL205 in dogs
FIG. 4: Zinc dependence of the hypoglycemic effect of YKL205 in dogs The following examples are intended to illustrate the concept of the invention without having a restrictive effect in this connection.

EXAMPLE 1

Preparation of the Vector Derivative pINT3580 which Codes for Gly (A21)-Insulin and a Modified C Peptide which Carries Arg Arg at the C/A Chain Boundary European patent application EP-A 1 222 207 describes the plasmids pINT358d, pINT91d and the primer sequence Tir. DNA of these products is used to construct the plasmid pINT3580. The plasmid pINT358d is moreover characterized by a gene sequence which codes for a modified C peptide having particular properties. Three primer sequences are synthesized:

```
pint3580_glya21rev
                                    (SEQ ID NO: 3)
5'-CAAAGGTCGACTATTAGCCGCAGTAGTTCTCCAGCTGG-3'
```

This primer serves after working up to introduce glycine (bold print, underlined) instead of asparagine in position 21 of the A chain of the proinsulin sequence encoded by pINT358d.

```
arg_cjuncf
                                    (SEQ ID NO: 4)
5'-GTCCCTGCAGCGTCGCGGCATCGTGGAGCAG-3'
```

This primer serves like the primer arg_cjunc_rev for introducing arginine instead of lysine at the insulin A/B chain boundary.

```
arg_cjunc_rev
                                    (SEQ ID NO: 5)
5'-CCACGATGCC GCGACGCTGC AGGGACCCCT CCAGCG-3'
```

The codon for the arginine to be introduced is in bold print in both primers. A PCR is carried out in accordance with the European patent application EP-A 1 222 207 with each of the primer pairs Tir/arg_cjunc_rev and arg_cjuncf/pint3580_glya21 rev and with DNA of the plasmid pINT358d as template. Aliquots of the products of the two reactions are combined and employed together with the primer pair Tir/pint3580_glya21 rev in a third PCR. The product of this reaction is purified after fractionation of the reaction mixture by gel electrophoresis and is digested with the restriction enzymes Sal1/Nco1 in accordance with the manufacturer's instructions in one and the same reaction, the reaction mixture is fractionated by gel electrophoresis, and the DNA fragment encoding the proinsulin sequence is isolated. The fragment is then inserted by a DNA ligase reaction into the Nco1/Sal1-opened pINT91d vector DNA.

The ligation mixture is used to transform competent *E. coli* bacterial cells. The transformation mixture is taken out on selection plates which contain 25 mg/l ampicillin. Plasmid DNA is isolated from colonies and characterized by DNA sequence analysis. Correct plasmids are called pINT3580.

EXAMPLE 2

Construction of the Plasmid pINT3581 Coding for His (A8), Gly (A21)—preproinsulin The construction takes place as described in example 1 by 3 polymerase chain reactions. The product of the third reaction is inserted after Nco1/Sal1 cleavage into the Nco1/Sal1-opened pINT91d vector DNA. The primers Tir and pint3580_glya21 rev are used. Two further primers are synthesized:

```
pint3580_Ha8f
                                    (SEQ ID NO: 6)
5'-AGCAGTGCTGCCACAGCATCTGCTCCCTCTAC-3' pint3580_Ha8rev
                                    (SEQ ID NO: 7)
5'-GAG CAGATGCT GTG GCAGCACTG CTCCACGATG-3'
```

The codon which codes for histidine in position 8 of the A chain is emphasized by emboldening in each case. The construction is carried out as described in example 1. Template for PCR1 and 2 is DNA of the plasmid pINT3580. PCR1 is carried out with the primer pair Tir/pint3580_Ha8rev and PCR2 is carried out with the primer pair pint3580_Ha8f/pint3580_glya21 rev. The primer pair Tir/pint3580_glya21 rev is employed in PCR 3. Template in this case is a mixture of the reaction products of PCR1 and PCR2. Correct plasmids are called pINT3581.

EXAMPLE 3

Construction of the Plasmid pINT3582 Coding for His (A8), Glu (A5), Gly (A21)—preproinsulin The construction takes place as described in example 1 and 2 by 3 polymerase chain reactions. The product of the third reaction is inserted after Nco1/Sal1 cleavage into the Nco1/Sal1-opened pINT91d vector DNA. The primers Tir and pint3580_glya21 rev are used. Two further primers are synthesized.

```
pint3581_Ea5f
                                    (SEQ ID NO: 8)
5'GCATCGTGGAGGAGTGCTGCCACAGCATCTG 3' pint3581_Ea5rev
                                    (SEQ ID NO: 9)
5'-CTGT GGCAGCACTC CTCCACGATG CCGCGACG-3'
```

The codon which codes for glutamic acid in position 5 of the A chain is emphasized by emboldening in each case. The construction is carried out as described in example 1. Template is DNA of the plasmid pINT3581. Correct plasmids are called pINT3582.

EXAMPLE 4

Construction of the Plasmid pINT3583 Coding for His (A8), Asp (A18), Gly(A21)—Preproinsulin The construction differs from example 1 by taking place by only one polymerase chain reaction. The product of this reaction is inserted after Nco1/Sal1 cleavage into the Nco1/Sal1-opened pINT91d vector DNA. The primer Tir is used. One further primer is synthesized:

pint3580_Da18rev
5' CAAAGGTCGACTATTAGCCGCAGTAGTCCTCCAGCTGGTAGAGGGAG 3' (SEQ ID NO: 10)

The codon which codes for aspartic acid in position 18 of the A chain is emphasized by emboldening. Template is DNA of the plasmid pINT3581. Correct plasmids are called pINT3583.

EXAMPLE 5

Construction of the Plasmid pINT3584 Coding for His (A8), Glu (A5) Asp (A18), Gly (A21)—Preproinsulin The construction differs from example 1 by taking place by only one polymerase chain reaction. The product of this reaction is inserted after Nco1/Sal1 cleavage into the Nco1/Sal1-opened pINT91d vector DNA. The primer Tir. pint3580_Da18rev (ex. 4) is used. Template is DNA of the plasmid pINT3582. Correct plasmids are called pINT3584. The preproinsulin encoded by the plasmid is precursor for the compound YKL205-1 which results after amidation with argininamide and describes the following structure:
Arg (A0), Glu (A5), His (A8), Asp(A18), Gly(A21), Arg (B31), Arg(B32)—NH$_2$—human insulin Corresponding amidation with lysinamide leads to the compound YKL205-1b:
Arg (A0), Glu (A5), His (A8), Asp (A18), Gly(A21), Arg (B31), Lys (B32)—NH$_2$—human insulin

EXAMPLE 6

Construction of the Plasmid pINT3585 Coding for His (A8), Glu (A15), Gly (A21)—Preproinsulin The construction differs from example 1 by taking place by only one polymerase chain reaction. The product of this reaction is inserted after Nco1/Sal1 cleavage into the Nco1/Sal1-opened pINT91d vector DNA. The primer Tir is used. One further primer is synthesized:

pint3580_Ea15rev
(SEQ ID NO: 11)
5'-CAAAGGTCGA CTATTAGCCG CAGTAGTTCTCCAGCTCGTA

GAGGGAGCAGATGCTG-3'

The codon which codes for glutamic acid in position 15 of the A chain is emphasized by emboldening. Template is DNA of the plasmid pINT3581. Correct plasmids are called pINT3585.

EXAMPLE 7

Construction of the Plasmid pINT3586 Coding for His (A8), Glu (A15), Asp (A18), Gly (A21)—Preproinsulin The construction differs from example 1 by taking place by only one polymerase chain reaction. The product of this reaction is inserted after Nco1/Sal1 cleavage into the Nco1/Sal1-opened pINT91d vector DNA. The primer Tir is used. One further primer is synthesized:

pint3585_Ea15_Da18rev
(SEQ ID NO: 12)
5'-CAAAGGTCGACTATTAGCCGCAGTAGTCCTCCAGCTCGTAGAGG

GAGCAGATGCTG-3'

The codon for glutamic acid in position 15 of the A chain and aspartic acid in position A18 of the A chain is emphasized by emboldening in each case. Template is DNA of the plasmid pINT3581. Correct plasmids are called pINT3586. The preproinsulin encoded by the plasmid is precursor for the compound YKL205 which results after amidation with argininamide and describes the following structure:
Arg (A0), His (A8), Glu (A15), Asp (A18), Gly (A21), Arg (B31), Arg (B32)—NH$_2$—human insulin The preproinsulin encoded by the plasmid is precursor for the compound YKL205b which results after amidation with lysinamide and describes the following structure:
Arg (A0), His (A8), Glu (A15), Asp (A18), Gly (A21), Arg (B31), Lys (B32)—NH$_2$—human insulin

EXAMPLE 8

Construction of the Plasmid pINT3587 Coding for Glu (A5), His (A8), Glu (A15), Gly (A21)—Preproinsulin The construction differs from example 1 by taking place by only one polymerase chain reaction. The product of this reaction is inserted after Nco1/Sal1 cleavage into the Nco1/Sal1-opened pINT91d vector DNA. The primer Tir and pint3580_Ea15rev shown in example 6 is used. Template is DNA of the plasmid pINT3582. Correct plasmids are called pINT3587. The preproinsulin encoded by the plasmid is precursor for the compound YKL205-2 which results after amidation with argininamide and describes the following structure:
Arg (A0), Glu (A5), His (A8), Glu (A15), Gly (A21), Arg (B31), Arg (B32)—NH$_2$—human insulin The preproinsulin encoded by the plasmid is precursor for the compound YKL205-2b which results after amidation with lysinamide and describes the following structure:
Arg (A0), Glu (A5), His (A8), Glu (A15), Gly (A21), Arg (B31), Lys (B32)—NH$_2$—human insulin

EXAMPLE 9

Construction of the Plasmid pINT3588 Coding for His (A8), Gly (A21), Asp (B3)—Preproinsulin Construction takes place as described in example 1 and 2 by 3 polymerase chain reactions. The product of the third reaction is inserted after Nco1/Sal1 cleavage into the Nco1/Sal1-opened pINT91d vector DNA. The primers Tir and pint3580_glya21 rev are used. Two further primers are synthesized:

pint3581_Db3f
(SEQ ID NO: 13)
5'-GCACGATTTGTGGACCAGCACCTGTGCGGC-3'

-continued

```
pint3581_Db3rev
                                            (SEQ ID NO: 14)
5'-CACAGG TGCTGGTCCA CAAATCGTGC CGAATTTC-3'
```

The codon which codes for aspartic acid in position 3 of the insulin B chain is emphasized by emboldening in each case. Construction is carried out as described in example 1. Template is DNA of the plasmid pINT3581. Correct plasmids are called pINT3588.

EXAMPLE 10

Construction of the Plasmid pINT3589 Coding for Glu (A5), His (A8), Gly (A21), Asp (B3)—Preproinsulin Carrying out the reactions as described in example 9 but using DNA of the plasmid pINT3582 as template in PCR1 and PCR2 results in plasmid pINT3589.

The preproinsulin encoded by the plasmid is precursor for the compound YKL205-3 which results after amidation with argininamide and describes the following structure:
Arg (A0), Glu (A5), His (A8), Gly (A21), Asp (B3), Arg (B31), Arg (B32)—NH$_2$—human insulin The preproinsulin encoded by the plasmid is precursor for the compound YKL205-3b which results after amidation with lysinamide and describes the following structure:
Arg (A0), Glu (A5), His (A8), Gly (A21), Asp (B3), Arg (B31), Lys (B32)—NH$_2$—human insulin

EXAMPLE 11

Construction of the Plasmid pINT3590 Coding for His (A8), Glu (A15), Gly (A21), Asp (B3)—Preproinsulin Carrying out the reactions as described in example 9 but using DNA of the plasmid pINT3585 as template in PCR1 and PCR2 results in plasmid pINT3590. The preproinsulin encoded by the plasmid is precursor for the compound YKL205-4 which results after amidation with argininamide and describes the following structure:
Arg (A0), His (A8), Glu (A15), Gly (A21), Asp (B3), Arg (B31), Arg (B32)—NH$_2$—human insulin The preproinsulin encoded by the plasmid is precursor for the compound YKL205-4-b which results after amidation with lysinamide and describes the following structure:
Arg (A0), His (A8), Glu (A15), Gly (A21), Asp (B3), Arg (B31), Lys (B32)—NH$_2$—human insulin

EXAMPLE 12

Construction of the Plasmid pINT3591 Coding for His (A8), Asp (A18), Gly (A21), Asp (B3)—Preproinsulin Carrying out the reactions as described in example 9 but using DNA of the plasmid pINT3586 as template in PCR1 and PCR2 results in plasmid pINT3591. The preproinsulin encoded by the plasmid is precursor for the compound YKL205-5 which results after amidation with argininamide and describes the following structure:
Arg (A0), His (A8), Asp (A18), Gly (A21), Asp (B3), Arg (B31), Arg (B32)—NH$_2$—human insulin The preproinsulin encoded by the plasmid is precursor for the compound YKL205-5b which results after amidation with lysinamide and describes the following structure:
Arg (A0), His (A8), Asp (A18), Gly (A21), Asp (B3), Arg (B31), Lys (B32)—NH$_2$—human insulin

EXAMPLE 13

Construction of the Plasmid pINT3592 Coding for His (A8), Gly (A21), Asp (B3)-Glu (B4)—Preproinsulin Construction takes place as described in example 1 and 2 by 3 polymerase chain reactions. The product of the third reaction is inserted after Nco1/Sal1 cleavage into the Nco1/Sal1-opened pINT91d vector DNA. The primers Tir and pint3580_glya21 rev are used. Two further primers are synthesized:

```
pint3581_Db3_Eb4f
                                            (SEQ ID NO: 15)
5'-GCACGATTTGTGGACGAGCACCTGTGCGGCTC-3' pint3581_Db3_Eb4rev
                                            (SEQ ID NO: 16)
5'-CGCACAGG TGCTCGTCCA CAAATCGTGC CGAATTTC-3'
```

The codon which codes for aspartic acid in position 3 and glutamic acid in position 4 of the insulin B chain is emphasized by emboldening in each case. The construction is carried out as described in example 1. Template is DNA of the plasmid pINT3581.

Correct plasmids are called pINT3592. The preproinsulin encoded by the plasmid is precursor for the compound YKL205-6 which results after amidation with argininamide and describes the following structure:
Arg (A0), His (A8), Gly (A21), Asp (B3), Glu (B4), Arg (B31), Arg (B32)—NH$_2$—human insulin The preproinsulin encoded by the plasmid is precursor for the compound YKL205-6b which results after amidation with lysinamide and describes the following structure:
Arg (A0), His (A8), Gly (A21), Asp (B3), Glu (B4), Arg (B31), Lys (B32)—NH$_2$—human insulin

EXAMPLE 14

Construction of the Plasmid pINT3593 Coding for His (A8), Gly (A21), Glu (B4)—Preproinsulin Construction takes place as described in example 1 and 2 by 3 polymerase chain reactions. The product of the third reaction is inserted after Nco1/Sal1 cleavage into the Nco1/Sal1-opened pINT91d vector DNA. The primers Tir and pint3580_glya21 rev are used. Two further primers are synthesized:

```
pint3581_Eb4f
                                            (SEQ ID NO: 17)
5'-ACGATTTGTGAACGAGCACCTGTGCGGCTC-3' pint3581_Eb4rev
                                            (SEQ ID NO: 18)
5'-CGCACAGG TGCTCGTTCA CAAATCGTGC CGAATTTC-3'
```

The codon which codes for glutamic acid in position 4 of the insulin B chain is emphasized by emboldening. The construction is carried out as described in example 1. Template is DNA of the plasmid pINT3581. Correct plasmids are called pINT3593.

EXAMPLE 15

Construction of the Plasmid pINT3594 Coding for Glu (A5), His (A8), Gly (A21), Glu (B4)—Preproinsulin Carrying out the reactions as described in example 9 but using DNA of the plasmid pINT3582 as template in PCR1 and PCR2 results in plasmid pINT3594.

The proinsulin is precursor for the compound YKL205-7 which results after amidation with argininamide and describes the following structure:
Arg (A0), Glu (A5), His (A8), Gly (A21), Glu (B4), Arg (B31), Arg (B32)—NH$_2$—human insulin.

The proinsulin is precursor for the compound YKL205-7b which results after amidation with lysinamide and describes the following structure:
Arg (A0), Glu (A5), His (A8), Gly (A21), Glu (B4), Arg (B31), Lys (B32)—NH$_2$—human insulin

EXAMPLE 16

Construction of the Plasmid pINT3595 Coding for His (A8), Glu (A15), Gly (A21), Glu (B4)—Preproinsulin Carrying out the reactions as described in example 9 but using DNA of the plasmid pINT3585 as template in PCR1 and PCR2 results in plasmid pINT3595. The preproinsulin encoded by the plasmid is precursor for the compound YKL205-8 which results after amidation with argininamide and describes the following structure:
Arg (A0), His (A8), Glu (A15), Gly (A21), Glu (B4), Arg (B31), Arg (B32)—NH$_2$—human insulin The preproinsulin encoded by the plasmid is precursor for the compound YKL205-8b which results after amidation with lysinamide and describes the following structure:
Arg (A0), His (A8), Glu (A15), Gly (A21), Glu (B4), Arg (B31), Lys (B32)—NH$_2$—human insulin

EXAMPLE 17

Construction of the Plasmid pINT3596 Coding for His (A8), Asp (A18), Gly (A21), Glu (B4)—Preproinsulin Carrying out the reactions as described in example 9 but using DNA of the plasmid pINT3586 as template in PCR1 and PCR2 results in plasmid pINT3596. The preproinsulin encoded by the plasmid is precursor for the compound YKL205-9 which results after amidation with argininamide and describes the following structure:
Arg (A0), His (A8), Asp (A18), Gly (A21), Glu (B4), Arg (B31), Arg (B32)—NH$_2$—human insulin The preproinsulin encoded by the plasmid is precursor for the compound YKL205-9b which results after amidation with lysinamide and describes the following structure:
Arg (A0), His (A8), Asp (A18), Gly (A21), Glu (B4), Arg (B31), Lys (B32)—NH$_2$—human insulin

EXAMPLE 18

Construction of the Plasmid pINT3597 Coding for His (A8), Gly (A21), Glu (B0)—Preproinsulin Construction takes place by 2 polymerase chain reactions. The primer pint3580_glya21rev is used. Two further primers are synthesized:

```
pint3581_Eb0f1
                                    (SEQ ID NO: 19)
5'-CAACAGGAA ATTCGGCACG AGAGTTTGTG AACCAGCACC
TGTG-3' pint3581_Eb01f2
                                    (SEQ ID NO: 20)
5'-TATCGA CCAT GG CAACAACA TCAACAGGAA ATTCGGCACG
AGAG-3'
```

There is partial overlap of the two primers in this case. Pint3581_Eb0f2 contains an NcoI recognition sequence. This is depicted underlined. The codon which codes for glutamic acid in position 0 at the start of the B chain is emphasized by emboldening in each case. Template for PCR1 is DNA of the plasmid pINT3581.

PCR1 is carried out with the primer pair pint3581_Eb-1f2/pint3580_glya21 rev. Template for PCR2 is the product from PCR1. PCR2 is carried out with the primer pair pint3581_Eb-1f2/pint3580_glya21 rev. The product from PCR2 covers the complete preproinsulin sequence. The product of the second reaction is inserted after Nco1/Sal1 cleavage into the Nco1/Sal1-opened pINT91d vector DNA. Correct plasmids are called pINT3597. Replacement of the codon for glutamic acid in position B0 by the codon of aspartic acid and following the example results in plasmids which have aspartic acid instead of glutamic acid in position B0.

EXAMPLE 19

Construction of the Plasmid pINT3598 Coding for Glu (A5), His (A8), Gly (A21), Glu (B0)—Preproinsulin Carrying out the reactions as described in example 18 but using DNA of the plasmid pINT3582 as template in PCR1 results in plasmid pINT3598. The preproinsulin encoded by the plasmid is precursor for the compound YKL205-10 which results after amidation with argininamide and describes the following structure:
Arg (A0), Glu (A5), His (A8), Gly (A21), Glu (B0), Arg (B31), Arg (B32)—NH$_2$—human insulin The preproinsulin encoded by the plasmid is precursor for the compound YKL205-10b which results after amidation with lysinamide and describes the following structure:
Arg (A0), Glu (A5), His (A8), Gly (A21), Glu (B0), Arg (B31), Lys (B32)—NH$_2$—human insulin

EXAMPLE 20

Construction of the Plasmid pINT3599 Coding for His (A8), Glu (A15), Gly (A21), Glu (B0)—Preproinsulin Carrying out the reactions as described in example 18 but using DNA of the plasmid pINT3585 as template in PCR1 results in plasmid pINT3599. The preproinsulin encoded by the plasmid is precursor for the compound YKL205-11 which results after amidation with argininamide and describes the following structure:
Arg (A0), His (A8), Glu (A15), Gly (A21), Glu (B0), Arg (B31), Arg (B32)—NH$_2$—human insulin The preproinsulin encoded by the plasmid is precursor for the compound YKL205-11b which results after amidation with lysinamide and describes the following structure:

Arg (A0), His (A8), Glu (A15), Gly (A21), Glu (B0), Arg (B31), Lys (B32)—NH$_2$—human insulin

EXAMPLE 21

Construction of the Plasmid pINT3600 Coding for His (A8), Asp (A18), Gly (A21), Glu (B0)—Preproinsulin Carrying out the reactions as described in example 18 but using DNA of the plasmid pINT3586 as template in PCR1 results in plasmid pINT3600. The preproinsulin encoded by the plasmid is precursor for the compound YKL205-12 which results after amidation with argininamide and describes the following structure:
Arg (A0), His (A8), Asp (A18), Gly (A21), Glu (B0), Arg (B31), Arg (B32)—NH$_2$—human insulin
The preproinsulin encoded by the plasmid is precursor for the compound YKL205-12b which results after amidation with lysinamide and describes the following structure:
Arg (A0), His (A8), Asp (A18), Gly (A21), Glu (B0), Arg (B31), Lys (B32)—NH$_2$—human insulin

EXAMPLE 22

Construction of the Plasmid pINT3601 Coding for His (A8), Gly (A21), Asp (B1)—preproinsulin Construction takes place by 2 polymerase chain reactions. The primer pint3580_glya21 rev is used. Two further primers are synthesized:

```
pint3581_Db1f1
                                       (SEQ ID NO: 21)
5'-CAACAGGAA ATTCGGCACG AGACGTG AACCAGCACC

TGTGCG-3' pint3581_Db1f2
                                       (SEQ ID NO: 22)
5'-TATCGA CCAT GG CAACAACA TCAACAGGAA ATTCGGCACG

AGAC-3'
```

There is partial overlap of the two primers in this case. Pint3581_Db-1f2 contains an NcoI recognition sequence. This is depicted underlined. The codon which codes for aspartic acid in position 1 of the B chain is emphasized by emboldening in each case. Template for PCR1 is DNA of the plasmid pINT3581. PCR1 is carried out with the primer pint3581_Db1f1/pint3580_glya21 rev. Template for PCR2 is the product from PCR1. PCR2 is carried out with the primer pair pint3581_Db1f2/pint3580_glya21 rev. The product from PCR2 covers the complete preproinsulin sequence. The product of the second reaction is inserted after Nco1/Sal1 cleavage into the Nco1/Sal1-opened pINT91d vector DNA. Correct plasmids are called pINT3601.

EXAMPLE 23

Construction of the Plasmid pINT3602 Coding for Glu (A5), His (A8), Gly (A21), Asp (B1)—preproinsulin Carrying out the reactions as described in example 22 by using DNA of the plasmid pINT3582 as template in PCR1 results in plasmid pINT3602. The preproinsulin encoded by the plasmid is precursor for the compound YKL205-13 which results after amidation with argininamide and describes the following structure:
Arg (A0), Glu (A5), His (A8), Gly (A21), Asp (B1), Arg (B31), Arg (B32)—NH$_2$—human insulin
The preproinsulin encoded by the plasmid is precursor for the compound YKL205-13b which results after amidation with lysinamide and describes the following structure:
Arg (A0), Glu (A5), His (A8), Gly (A21), Asp (B1), Arg (B31), Lys (B32)—NH$_2$—human insulin

EXAMPLE 24

Construction of the Plasmid pINT3603 Coding for His (A8), Glu (A15), Gly (A21), Asp (B1)—Preproinsulin Carrying out the reactions as described in example 22 by using DNA of the plasmid pINT3585 as template in PCR1 results in plasmid pINT3603. The preproinsulin encoded by the plasmid is precursor for the compound YKL205-14 which results after amidation with argininamide and describes the following structure:
Arg (A0), His (A8), Glu (A15), Gly (A21), Asp (B1), Arg (B31), Arg (B32)—NH$_2$—human insulin
The preproinsulin coded by the plasmid is precursor for the compound YKL205-14b which results after amidation with lysinamide and describes the following structure:
Arg (A0), His (A8), Glu (A15), Gly (A21), Asp (B1), Arg (B31), Lys (B32)—NH$_2$—human insulin

EXAMPLE 25

Construction of the Plasmid pINT3604 Coding for His (A8), Asp (A18), Gly (A21), Asp (B1)—Preproinsulin Carrying out the reactions as described in example 22 but using DNA of the plasmid pINT3586 as template in PCR1 results in plasmid pINT3604. The preproinsulin encoded by the plasmid is precursor for the compound YKL205-15 which results after amidation with argininamide and describes the following structure:
Arg (A0), His (A8), Asp (A18), Gly (A21), Asp (B1), Arg (B31), Arg (B32)—NH$_2$—human insulin
The preproinsulin encoded by the plasmid is precursor for the compound YKL205-15b which results after amidation with lysinamide and describes the following structure:
Arg (A0), His (A8), Asp (A18), Gly (A21), Asp (B1), Arg (B31), Lys (B32)—NH$_2$—human insulin

EXAMPLE 26

Construction of the Plasmid pINT3605 Coding for His (A8), Gly (A21), Glu (B0), Asp (B1)—Preproinsulin Construction takes place by 2 polymerase chain reactions. The primer pint3580_glya21rev and the primer pint3581_Eb01f2 described in example 18 are used. The primer pint3597_Db1f is synthesized:

```
                                       (SEQ ID NO: 23)
5'-CAACAGGAA ATTCGGCACG AGAGGACGTG AACCAGCACC

TGTGC-3'
```

The codon which codes for glutamic acid in position 0 and which codes for aspartic acid in each case at the start of the B chain is emphasized by emboldening in each case. Template for PCR1 is DNA of the plasmid pINT3597. PCR1 is carried out with the primer pair pint3597_Dblf/pint3580_glya21 rev. Template for PCR2 is the product from PCR1. PCR2 is carried out with the primer pair pint3581_Eblf2/pint3580_glya21 rev. The product from PCR2 covers the complete preproinsulin sequence. The product of the second reaction is inserted after Nco1/Sal1 cleavage into the Nco1/Sal1-opened pINT91d vector DNA. Correct plasmids are called pINT3605. The preproinsulin encoded by the plasmid is precursor for the compound YKL205-16 which results after amidation with argininamide and describes the following structure:

Arg (A0), His (A8), Gly (A21), Glu (B0), Asp (B1), Arg (B31), Arg (B32)—$NH_2$—human insulin The preproinsulin encoded by the plasmid is precursor for the compound YKL205-16a which results after amidation with lysinamide and describes the following structure:

Arg (A0), His (A8), Gly (A21), Glu (B0), Asp (B1), Arg (B31), Lys (B32)—$NH_2$—human insulin

EXAMPLE 27

Construction of the Plasmid pINT3606 Coding for His (A8), Glu (A15), Asp (A18), Gly (A21), desThr (B30)—Preproinsulin Construction takes place as described in example 1 and 2 by 3 polymerase chain reactions. The primers Tir and pint3580_glya21 rev are used. Two further primers are synthesized:

```
desB30f
                                          (SEQ ID NO: 24)
5'-TTCTACACACCCAAGCGCGATGTTCCTCAGGTGG-3' desB30rev
                                          (SEQ ID NO: 25)
5'-AGG AACATCGCGC TTGGGTGTGT AGAAGAAGC-3'
```

Template for PCR1 and PCR2 is DNA of the plasmid pINT3586. PCR1 is carried out with the primer pair desB30f/pint3580_glya21 rev and PCR2 is carried out with the primer pair Tir/desB30rev template. The template used for PCR3 is an equimolar mixture of the products from PCR1 and PCR2. The reaction is carried out with the primer pair Tir/pint3580_glya21 rev. The product from PCR3 covers the complete preproinsulin sequence. The product of the third reaction is inserted after Nco1/Sal1 cleavage into the Nco1/Sal1-opened pINT91d vector DNA. The preproinsulin encoded by the plasmid is precursor for the compound YKL205-17 which results after amidation with argininamide and describes the following structure:

Arg (A0), His (A8), Glu (A15), Asp (A18), Gly (A21), Arg (B30), Arg (B31)—$NH_2$—human insulin The preproinsulin encoded by the plasmid is precursor for the compound YKL205-17b which results after amidation with lysinamide and describes the following structure:

Arg (A0), His (A8), Glu (A15), Asp (A18), Gly (A21), Arg (B30), Lys (B31)—$NH_2$—human insulin

EXAMPLE 28

Expression of the Proinsulin Derivatives

The expression is carried out in accordance with example 1 of European patent application EP-A 1 222 207.

EXAMPLE 29

Folding of the Proinsulin Derivatives

The folding takes place in principle by the method described in EP-A 0 668 282

EXAMPLE 30

Enzymatic Processing of the Folded Preproinsulin to Give the 2-chain Arg(A0)—Insulin Precursor whose C-terminal B Chain End is Characterized by Lysine or Arginine The enzymatic processing of the folded preproinsulin precursor takes place as described for example in example 4 of WO91/03550. It proves to be particularly advantageous in this case to employ the trypsin variant described in WO 2007/031187 A1.

EXAMPLE 31

Preparation of an Arg (A0), His (A8), Gly (A21), Arg (B31), Arg (B32)—$NH_2$-human Insulin Irrespective of the positioning of the additional acidic amino acids, a standard reaction is carried out as follows: 100 mg of Arg (A0), Gly (A21), Arg (B31)—insulin analogue are dissolved in 0.95 ml of argininamide solution (446 g/L), and 0.13 mL of M Na acetate buffer (pH 5.8) and 2 ml of DMF are added. The reaction mixture is cooled to 12° C. and started by adding 0.094 ml of trypsin (0.075 mg, Roche Diagnostics). The reaction is stopped after 8 h by adding TFA to pH 2.5 and analyzed by HPLC. There is formation of >60% Arg (A0), Gly (A21), Arg (B31), Arg (B32)—$NH_2$— human insulin. Addition of trypsin inhibitor solution is followed by purification of the amidated analogue in analogy to U.S. Pat. No. 5,656,722.

Preparation of the corresponding lysinamide compound takes place analogously. However, an aqueous lysinamide stock solution containing 366 g/L lysinamide in solution forms the starting material.

EXAMPLE 32

Formulation of the Amidated Insulin Derivatives

In order to test the insulin derivatives of the invention for their biopharmacological and physicochemical properties, a solution of the compounds was prepared as follows: the insulin derivative of the invention was dissolved with a target concentration of 240±5 µM in 1 mM hydrochloric acid with 80 µg/mL zinc (as zinc chloride).

The following compositions were used as dissolving medium:
a) 1 mM hydrochloric acid
b) 1 mM hydrochloric acid, 5 µg/ml zinc (added as zinc chloride or hydrochloric acid)
c) 1 mM hydrochloric acid, 10 µg/ml zinc (added as zinc chloride or hydrochloric acid)

d) 1 mM hydrochloric acid, 15 µg/ml zinc (added as zinc chloride or hydrochloric acid)
e) 1 mM hydrochloric acid, 30 µg/ml zinc (added as zinc chloride or hydrochloric acid)
f) 1 mM hydrochloric acid, 80 µg/ml zinc (added as zinc chloride or hydrochloric acid)
g) 1 mM hydrochloric acid, 120 µg/ml zinc (added as zinc chloride or hydrochloric acid)

For this purpose, initially an amount of the freeze-dried material which is about 30% higher than required on the basis of the molecular weight and the desired concentration was weighed out. The concentration present was then determined by analytical HPLC and the solution was subsequently made up to the volume necessary to achieve the target concentration with 5 mM hydrochloric acid with 80 µg/mL zinc. If necessary, the pH was readjusted to 3.5±0.1. After the final analysis by HPLC to verify the target concentration of 240±5 µM, the finished solution was transferred by means of a syringe with a 0.2 µm filter attachment into a sterile vial which was closed with a septum and a crimped cap. No optimization of the formulations, e.g. in relation to addition of isotonic agents, preservatives or buffer substances, was carried out for the short-term single testing of the insulin derivatives of the invention.

EXAMPLE 33

Evaluation of the Blood Glucose-lowering Effect of Novel Insulin Analogues in Rats The blood glucose-lowering effect of selected novel insulin analogues is tested in healthy male normoglycemic Wistar rats. Male rats receive subcutaneous injection of a dose of 9 nmol/kg of an insulin analogue. Blood samples are taken from the animals immediately before the injection of the insulin analogue and at regular intervals up to eight hours after the injection, and the blood glucose content therein is determined. The experiment shows clearly (cf. FIG. 1) that the employed insulin analogue of the invention leads to a distinctly delayed onset of action and a longer, uniform duration of action.

EXAMPLE 34

Evaluation of the Blood Glucose-lowering Effect of Novel Insulin Analogues in Dogs The blood glucose-lowering effect of selected novel insulin analogues is tested in healthy male normoglycemic beagle dogs. Male animals receive subcutaneous injection of a dose of 6 nmol/kg of an insulin analogue. Blood samples are taken from the animals immediately before the injection of the insulin analogue and at regular intervals up to 48 hours after the injection, and the blood glucose content therein is determined. The experiment shows clearly (cf. FIG. 2) that the employed insulin analogue of the invention leads to a distinctly delayed onset of action and a longer, uniform duration of action.

EXAMPLE 35

Evaluation of the Blood Glucose-lowering Effect in Dogs with a Dose Increased Two-fold The blood glucose-lowering effect of selected novel insulin analogues is tested in healthy male normoglycemic beagle dogs. Male animals receive subcutaneous injection of a dose of 6 nmol/kg and 12 nmol/kg of an insulin analogue. Blood samples are taken from the animals immediately before the injection of the insulin analogue and at regular intervals up to 48 hours after the injection, and the blood glucose content therein is determined. The experiment shows clearly (cf. FIG. 3) that the employed insulin analogue of the invention has a dose-dependent effect but that, despite the dose being increased two-fold, the action profile has a shallow profile, i.e. no pronounced low point (nadir) is observed. It can be deduced from this that the insulins of the invention lead to distinctly fewer hypoglycemic events by comparison with known slow insulins.

EXAMPLE 36

Figure 4:
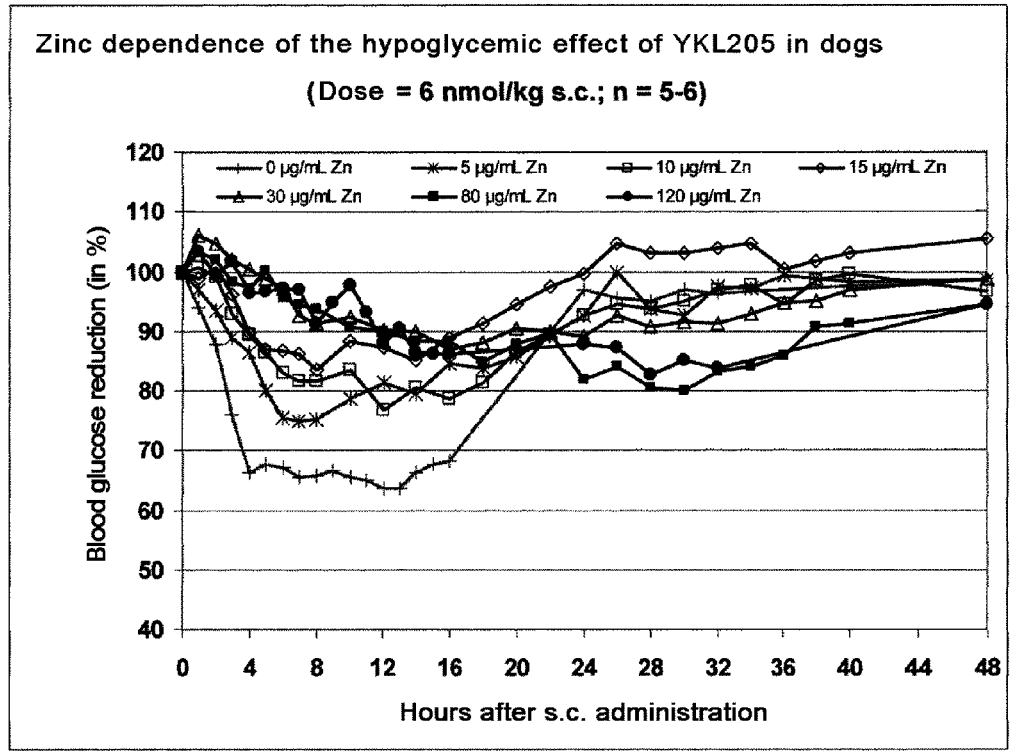
FIG. 4 shows zinc dependence of the hypoglycemic effect of YKL205 in dogs (Dose=6 nmol/kg s.c.; n=5-6)

Evaluation of the Blood Glucose-lowering Effect in Dogs with Different Zinc Concentrations in the Formulation The experiments were carried out as described in Example 35. FIG. 4 shows the result. According to this, the time-effect curve of the insulin analogue of the invention can be influenced through the content of zinc ions in the formulation with the same insulin concentration in such a way that a rapid onset of action is observed with a zero or low zinc content, and the effect is maintained for 24 hours, whereas a gradual onset of action is observed with a higher zinc content, and the insulin effect is maintained for distinctly longer than 24 hours.

What is claimed is:

1. An insulin analogue of the formula:

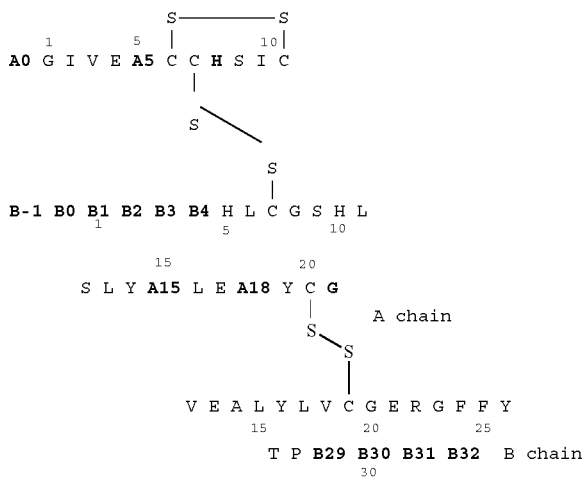

wherein
- A0 corresponds to Lys or Arg;
- A5 corresponds to Asp, Gln or Glu;
- A15 corresponds to Asp, Glu or Gln;
- A18 corresponds to Asp, Glu or Asn;
- B-1 corresponds to Asp, Glu;
- B0 corresponds to Asp, Glu or a chemical bond;
- B1 corresponds to Asp, Glu or Phe;
- B2 corresponds to Asp, Glu or Val;
- B3 corresponds to Asp, Glu or Asn;
- B4 corresponds to Asp, Glu or Gln;
- B29 corresponds to Lys or a chemical bond;
- B30 corresponds to Thr or a chemical bond;
- B31 corresponds to Arg, Lys or a chemical bond;
- B32 corresponds to Arg-amide or Lys-amide; and wherein two amino acid residues of the group comprising A5, A15, A18, B-1, B0, B1, B2, B3 and B4 correspond simultaneously and independently of one another to Asp or Glu.

2. The insulin analogue as claimed in claim 1, wherein A0 corresponds to Arg.

3. The insulin analogue as claimed in claim 1, wherein A5 corresponds to Glu.

4. The insulin analogue as claimed in claim 1, wherein A15 corresponds to Glu.

5. The insulin analogue as claimed in claim 1, wherein A18 corresponds to Asp.

6. The insulin analogue as claimed in claim 1, wherein B0 corresponds to Glu.

7. The insulin analogue as claimed in claim 1, wherein B1 corresponds to Asp.

8. The insulin analogue as claimed in claim 1, wherein B2 corresponds to Val.

9. The insulin analogue as claimed in claim 1, wherein B3 corresponds to Asp.

10. The insulin analogue as claimed in claim 1, wherein B4 corresponds to Glu.

11. The insulin analogue as claimed in claim 1, wherein B29 corresponds to Lys.

12. The insulin analogue as claimed in claim 1, wherein B30 corresponds to Thr.

13. The insulin analogue as claimed in claim 1, wherein B31 corresponds to Arg or Lys.

14. The insulin analogue as claimed in claim 1, selected from the group consisting of:
- Arg (A0), His (A8), Glu (A5), Gly (A21), Glu (B1), Arg (B31), Arg (B32)—NH$_2$ human insulin;
- Arg (A0), His (A8), Glu (A5), Gly (A21), Glu (B1), Arg (B31), Lys (B32)—NH$_2$ human insulin;,
- Arg (A0), His (A8), Glu (A15), Gly (A21), Glu (B1), Arg (B31), Arg (B32)—NH$_2$ human insulin;
- Arg (A0), His (A8), Glu (A15), Gly (A21), Glu (B1), Arg (B31), Lys (B32)—NH$_2$ human insulin;
- Arg (A0), His (A8), Asp (A18), Gly (A21), Glu (B1), Arg (B31), Arg (B32)—NH$_2$ human insulin;
- Arg (A0), His (A8), Gly (A21), Glu (B1), Asp (B1), Arg (B31), Arg (B32)—NH$_2$ human insulin; and
- Arg (A0), His (A8), Gly (A21), Glu (B1), Asp (B1), Arg (B31), Lys (B32)—NH$_2$ human insulin.

15. A process for preparing an insulin analogue as claimed in claim 1, comprising the steps of:
(a) recombinantly preparing a precursor of the insulin analogue;
(b) enzymatically processing the precursor to two-chain insulin;
(c) coupling the two-chain insulin to argininamide in the presence of an enzyme having trypsin activity to produce the insulin analogue; and
(d) isolating the insulin analogue.

16. A method of making a medicament for treating diabetes mellitus, the method comprising combining the insulin analogue of claim 1 with one or more pharmaceutically acceptable ingredients.

17. The method of making of claim 16, wherein the medicament is for the treatment of diabetes mellitus of type I or type II or for therapeutically assisting beta cell regeneration.

18. A pharmaceutical composition comprising the insulin analogue of claim 1 or a physiologically acceptable salt thereof.

19. A formulation of the insulin analogue of claim 1, wherein the formulation is in aqueous form comprising the dissolved insulin analogue.

20. A formulation of the insulin analogue of claim 1, wherein the formulation is in the form of a powder.

21. The formulation of claim 20, wherein the insulin analogue is present in crystalline or amorphous form.

22. A formulation of the insulin analogue of claim 1, wherein the formulation is in the form of a suspension.

23. A formulation of the insulin analogue of claim 1, wherein the formulation further comprises a chemical chaperone.

24. The formulation of claim 19, further comprises a glucagon-like peptide-1 (GLP1) or an analogue or derivative thereof, exendin-3 or an analogue or derivative thereof, or exendin-4 or an analogue or derivative therof.

25. The formulation of 20, further comprises a glucagon-like peptide-1 (GLP1) or an analogue or derivative thereof, exendin-3 or an analogue or derivative thereof, or exendin-4 or an analogue or derivative thereof.

26. The formulation of claim 21, further comprises a glucagon-like peptide-1 (GLP1) or an analogue or derivative thereof, exendin-3 or an analogue or derivative thereof, or exendin-4 or an analogue or derivative thereof.

27. The formulation of claim 22, further comprises a glucagon-like peptide-1 (GLP1) or an analogue or derivative thereof, exendin-3 or an analogue or derivative thereof, or exendin-4 or an analogue or derivative thereof.

28. The formulation of claim 23, further comprises a glucagon-like peptide-1 (GLP1) or an analogue or derivative thereof, exendin-3 or analogue or derivative thereof, or exendin-4 or an analogue or derivative thereof.

29. The formulation of claim 24, wherein the formulation comprises exendin-4 or an analogue or derivative thereof.

30. The formulation of claim 29, wherein the exendin-4 analogue is selected from a group comprising of:
    H-desPro$^{36}$-exendin-4-Lys$_6$—NH$_2$,
    H-des(Pro$^{36,37}$)-exendin-4-Lys$_4$—NH$_2$, and
    H-des(Pro$^{36,37}$)-exendin-4-Lys$_5$—NH$_2$,
    or a pharmacologically tolerable salt thereof.

31. The formulation of claim 29, wherein the exendin-4 analogue is selected from a group comprising of:
    desPro$^{36}$ [Asp$^{28}$]exendin-4 (1-39),
    desPro$^{36}$ [IsoAsp$^{28}$]exendin-4 (1-39),
    desPro$^{36}$ [Met(O)$^{14}$, Asp$^{28}$]exendin-4 (1-39),
    desPro$^{36}$ [Met(O)$^{14}$, IsoAsp$^{28}$]exendin-4 (1-39),
    desPro$^{36}$ [Trp(O$_2$)$^{25}$, Asp$^{28}$]exendin-4 (1-39),
    desPro$^{36}$ [Trp(O$_2$)$^{25}$, IsoAsp$^{28}$]exendin-4 (1-39),
    desPro$^{36}$ [Met(O)$^{14}$Trp(O$_2$)$^{25}$, Asp$^{28}$]exendin-4 (1-39) and
    desPro$^{36}$ [Met(O)$^{14}$Trp(O$_2$)$^{25}$, IsoAsp$^{28}$]exendin-4 (1-39),
    or a pharmacologically tolerable salt thereof.

32. The formulation of claim 31, where the peptide -Lys$_6$—NH$_2$ is attached to the C terminus of the exendin-4 analogue.

33. The formulation of claim 24, wherein the exendin-4 analogue is selected from the group comprising of:
    H-(Lys)$_6$-des Pro$^{36}$ [Asp$^{28}$]exendin-4(1-39)-Lys$_6$-NH$_2$;
    des Asp$^{28}$Pro$^{36}$, Pro$^{37}$, Pro$^{38}$ exendin-4(1-39)—NH$_2$;
    H-(Lys)$_6$-des Pro$^{36}$, Pro$^{37}$, Pro$^{38}$ [Asp$^{28}$]exendin-4(1-39)—NH$_2$;
    H-Asn-(Glu)$_5$ des Pro$^{36}$, Pro$^{37}$, Pro$^{38}$ [Asp$^{28}$]exendin-4(1-39)—NH$_2$;
    des Pro$^{36}$, Pro$^{37}$, Pro$^{38}$ [Asp$^{28}$]exendin-4(1-39)-(Lys)$_6$—NH$_2$;
    H-(Lys)$_6$-des Pro$^{36}$, Pro$^{37}$, Pro$^{38}$ [Asp$^{28}$]exendin-4(1-39)-(Lys)$_6$—NH$_2$;
    H-Asn-(Glu)$_5$-des Pro$^{36}$, Pro$^{37}$, Pro$^{38}$ [Asp$^{28}$]exendin-4(1-39)-(Lys)$_6$—NH$_2$;
    H-(Lys)$_6$-des Pro$^{36}$ [Trp(O$_2$)$^{25}$, Asp$^{28}$]exendin-4(1-39)-Lys$_6$—NH$_2$;
    H-des Asp$^{28}$ Pro$^{36}$, Pro$^{37}$, Pro$^{38}$ [Trp(O$_2$)$^{25}$]exendin-4(1-39)—NH$_2$;
    H-(Lys)$_6$-des Pro$^{36}$, Pro$^{37}$, Pro$^{38}$ [TrP(O$_2$)$^{25}$, Asp$^{28}$]exendin-4(1-39)—NH$_2$;
    H-Asn-(Glu)$_5$-des Pro$^{36}$, Pro$^{37}$, Pro$^{38}$ [Trp(O$_2$)$^{25}$, Asp$^{28}$] exendin-4(1-39)—NH$_2$;
    des Pro$^{36}$, Pro$^{37}$, Pro$^{38}$ [Trp(O$_2$)$^{25}$, Asp$^{28}$]exendin-4(1-39)-(Lys)$_6$—NH$_2$;
    H-(Lys)$_6$-des Pro$^{36}$, Pro$^{37}$, Pro$^{38}$ [TrP(O$_2$)$^{25}$, Asp$^{28}$]exendin-4(1-39)-(Lys)$_6$—NH$_2$;
    H-Asn-(Glu)$_5$-des Pro$^{36}$, Pro$^{37}$, Pro$^{38}$ [Trp(O$_2$)$^{25}$, Asp$^{28}$] exendin-4(1-39)-(Lys)$_6$—NH$_2$;
    H-(Lys)$_6$-des Pro$^{36}$ [Met(O)$^{14}$, Asp$^{28}$]exendin-4(1-39)-Lys$_6$—NH$_2$;
    des Met(O)$^{14}$ Asp$^{28}$ Pro$^{36}$, Pro$^{37}$, Pro$^{38}$ exendin-4(1-39)—NH$_2$;
    H-(Lys)$_6$-des Pro$^{36}$, Pro$^{37}$, Pro$^{38}$ [Met(O)$^{14}$, Asp$^{28}$]exendin-4(1-39)—NH$_2$;
    H-Asn-(Glu)$_5$-des Pro$^{36}$, Pro$^{37}$, Pro$^{38}$ [Met(O)$^{14}$, Asp$^{28}$] exendin-4(1-39)—NH$_2$;
    des Pro$^{36}$, Pro$^{37}$, Pro$^{38}$ [Met(O)$^{14}$, Asp$^{28}$]exendin-4(1-39)-(Lys)$_6$—NH$_2$;
    H-(Lys)$_6$-des Pro$^{36}$, Pro$^{37}$, Pro$^{38}$ [Met(O)$^{14}$, Asp$^{28}$]exendin-4(1-39)-Lys$_6$—NH$_2$;
    H-Asn-(Glu)$_5$ des Pro$^{36}$, Pro$^{37}$, Pro$^{38}$ [Met(O)$^{14}$, Asp$^{28}$] exendin-4(1-39)-(Lys)$_6$—NH$_2$;
    H-(Lys)$_6$-des Pro$^{36}$ [Met(O)$^{14}$, Trp(O$_2$)$^{25}$, Asp$^{28}$]exendin-4(1-39)-Lys$_6$—NH$_2$;
    des Asp$^{28}$ Pro$^{36}$, Pro$^{37}$, Pro$^{38}$ [Met(O)$^{14}$, Trp(O$_2$)$^{25}$]exendin-4(1-39)—NH$_2$;
    H-(Lys)$_6$-des Pro$^{36'}$ Pro$^{37}$, Pro$^{38}$ [Met(O)$^{14}$, Trp(O$_2$)$^{25}$, Asp$^{28}$]exendin-4(1-39)—NH$_2$;
    H-Asn-(Glu)$_5$-des Pro$^{36}$, Pro$^{37}$, Pro$^{38}$ [Met(O)$^{14}$, Asp$^{28}$] exendin-4(1-39)—NH$_2$;
    des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$—NH$_2$;
    H-(Lys)$_6$-des Pro$^{36'}$ Pro$^{37}$, Pro$^{38}$ [Met(O)$^{14}$, Trp(O$_2$)$^{25}$, Asp$^{28}$]exendin-4(1-39)-(Lys)$_6$—NH$_2$; and
    H-Asn-(Glu)$_5$-des Pro$^{36}$, Pro$^{37}$, Pro$^{38}$ [Met(O)$^{14}$, Trp(O$_2$)$^{25}$, Asp$^{28}$] exendin-4(1-39) -(Lys)$_6$—NH$_2$;
    or a pharmacologically tolerable salt thereof.

34. The formulation of claim 24, further comprising Arg$^{34}$, Lys$^{26}$ (N$^\epsilon$(γ-glutamyl(N$^\alpha$-hexadecanoyl))) GLP-1 (7-37) [liraglutide] or a pharmacologically tolerable salt thereof.

35. An aqueous formulation comprising the insulin analogue of claim 1, which comprises less than 15 µg/ml of zinc.

36. An aqueous formulation comprising the insulin analogue of claim 1, which comprises less than 2 mg/ml of zinc.

37. The aqueous formulation of claim 36, which comprises 200 µg/ml of zinc.

* * * * *

SEQUENCE LISTING

```
<160> NUMBER OF SEQ ID NOS: 25

<210> SEQ ID NO 1
<211> LENGTH: 22
<212> TYPE: PRT
<213> ORGANISM: Artificial Sequence
<220> FEATURE:
<223> OTHER INFORMATION: A-Chain
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
```

```
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 1

Xaa Gly Ile Val Glu Xaa Cys Cys His Ser Ile Cys Ser Leu Tyr Xaa
1               5                  10                  15

Leu Glu Xaa Tyr Cys Gly
            20

<210> SEQ ID NO 2
<211> LENGTH: 34
<212> TYPE: PRT
<213> ORGANISM: Artificial Sequence
<220> FEATURE:
<223> OTHER INFORMATION: B-Chain
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (31)..(34)
<223> OTHER INFORMATION: Xaa can be any naturally occurring amino acid

<400> SEQUENCE: 2

Xaa Xaa Xaa Xaa Xaa Xaa His Leu Cys Gly Ser His Leu Val Glu Ala
1               5                  10                  15

Leu Tyr Leu Val Cys Gly Glu Arg Gly Phe Phe Tyr Thr Pro Xaa Xaa
            20                  25                  30

Xaa Xaa

<210> SEQ ID NO 3
<211> LENGTH: 38
<212> TYPE: DNA
<213> ORGANISM: Artificial Sequence
<220> FEATURE:
<223> OTHER INFORMATION: pint3580_glya21rev

<400> SEQUENCE: 3
caaaggtcga ctattagccg cagtagttct ccagctgg                              38

<210> SEQ ID NO 4
<211> LENGTH: 31
<212> TYPE: DNA
<213> ORGANISM: Artificial Sequence
<220> FEATURE:
<223> OTHER INFORMATION: arg_cjuncf

<400> SEQUENCE: 4
gtccctgcag cgtcgcggca tcgtggagca g                                     31

<210> SEQ ID NO 5
<211> LENGTH: 36
<212> TYPE: DNA
<213> ORGANISM: Artificial Sequence
<220> FEATURE:
<223> OTHER INFORMATION: arg_cjunc_rev

<400> SEQUENCE: 5
ccacgatgcc gcgacgctgc agggacccct ccagcg                                36
```

```
<210> SEQ ID NO 6
<211> LENGTH: 32
<212> TYPE: DNA
<213> ORGANISM: Artificial Sequence
<220> FEATURE:
<223> OTHER INFORMATION: pint3580_Ha8f

<400> SEQUENCE: 6
agcagtgctg ccacagcatc tgctccctct ac                                32

<210> SEQ ID NO 7
<211> LENGTH: 33
<212> TYPE: DNA
<213> ORGANISM: Artificial Sequence
<220> FEATURE:
<223> OTHER INFORMATION: pint3580_Ha8rev

<400> SEQUENCE: 7
gagcagatgc tgtggcagca ctgctccacg atg                               33

<210> SEQ ID NO 8
<211> LENGTH: 31
<212> TYPE: DNA
<213> ORGANISM: Artificial Sequence
<220> FEATURE:
<223> OTHER INFORMATION: pint3581_Ea5f

<400> SEQUENCE: 8
gcatcgtgga ggagtgctgc cacagcatct g                                 31

<210> SEQ ID NO 9
<211> LENGTH: 32
<212> TYPE: DNA
<213> ORGANISM: Artificial Sequence
<220> FEATURE:
<223> OTHER INFORMATION: pint3581_Ea5rev

<400> SEQUENCE: 9
ctgtggcagc actcctccac gatgccgcga cg                                32

<210> SEQ ID NO 10
<211> LENGTH: 47
<212> TYPE: DNA
<213> ORGANISM: Artificial Sequence
<220> FEATURE:
<223> OTHER INFORMATION: pint3580_Da18rev

<400> SEQUENCE: 10
caaaggtcga ctattagccg cagtagtcct ccagctggta gagggag                47

<210> SEQ ID NO 11
<211> LENGTH: 56
<212> TYPE: DNA
<213> ORGANISM: Artificial Sequence
<220> FEATURE:
<223> OTHER INFORMATION: pint3580_Ea15rev

<400> SEQUENCE: 11
caaaggtcga ctattagccg cagtagttct ccagctcgta gagggagcag atgctg      56

<210> SEQ ID NO 12
<211> LENGTH: 56
<212> TYPE: DNA
<213> ORGANISM: Artificial Sequence
<220> FEATURE:
<223> OTHER INFORMATION: pint3585_Ea15_Da18rev
```

<400> SEQUENCE: 12
caaaggtcga ctattagccg cagtagtcct ccagctcgta gagggagcag atgctg        56

<210> SEQ ID NO 13
<211> LENGTH: 30
<212> TYPE: DNA
<213> ORGANISM: Artificial Sequence
<220> FEATURE:
<223> OTHER INFORMATION: pint3581_Db3f

<400> SEQUENCE: 13
gcacgatttg tggaccagca cctgtgcggc        30

<210> SEQ ID NO 14
<211> LENGTH: 34
<212> TYPE: DNA
<213> ORGANISM: Artificial Sequence
<220> FEATURE:
<223> OTHER INFORMATION: pint3581_Db3rev

<400> SEQUENCE: 14
cacaggtgct ggtccacaaa tcgtgccgaa tttc        34

<210> SEQ ID NO 15
<211> LENGTH: 32
<212> TYPE: DNA
<213> ORGANISM: Artificial Sequence
<220> FEATURE:
<223> OTHER INFORMATION: pint3581_Db3_Eb4f

<400> SEQUENCE: 15
gcacgatttg tggacgagca cctgtgcggc tc        32

<210> SEQ ID NO 16
<211> LENGTH: 36
<212> TYPE: DNA
<213> ORGANISM: Artificial Sequence
<220> FEATURE:
<223> OTHER INFORMATION: pint3581_Db3_Eb4rev

<400> SEQUENCE: 16
cgcacaggtg ctcgtccaca aatcgtgccg aatttc        36

<210> SEQ ID NO 17
<211> LENGTH: 30
<212> TYPE: DNA
<213> ORGANISM: Artificial Sequence
<220> FEATURE:
<223> OTHER INFORMATION: pint3581_Eb4f

<400> SEQUENCE: 17
acgatttgtg aacgagcacc tgtgcggctc        30

<210> SEQ ID NO 18
<211> LENGTH: 36
<212> TYPE: DNA
<213> ORGANISM: Artificial Sequence
<220> FEATURE:
<223> OTHER INFORMATION: pint3581_Eb4rev

<400> SEQUENCE: 18
cgcacaggtg ctcgttcaca aatcgtgccg aatttc        36

<210> SEQ ID NO 19
<211> LENGTH: 43

<212> TYPE: DNA
<213> ORGANISM: Artificial Sequence
<220> FEATURE:
<223> OTHER INFORMATION: pint3581_Eb0f1

<400> SEQUENCE: 19
caacaggaaa ttcggcacga gagtttgtga accagcacct gtg                43

<210> SEQ ID NO 20
<211> LENGTH: 44
<212> TYPE: DNA
<213> ORGANISM: Artificial Sequence
<220> FEATURE:
<223> OTHER INFORMATION: pint3581_Eb01f2

<400> SEQUENCE: 20
tatcgaccat ggcaacaaca tcaacaggaa attcggcacg agag                44

<210> SEQ ID NO 21
<211> LENGTH: 42
<212> TYPE: DNA
<213> ORGANISM: Artificial Sequence
<220> FEATURE:
<223> OTHER INFORMATION: pint3581_Db1f1

<400> SEQUENCE: 21
caacaggaaa ttcggcacga gacgtgaacc agcacctgtg cg                42

<210> SEQ ID NO 22
<211> LENGTH: 44
<212> TYPE: DNA
<213> ORGANISM: Artificial Sequence
<220> FEATURE:
<223> OTHER INFORMATION: pint3581_Db1f2

<400> SEQUENCE: 22
tatcgaccat ggcaacaaca tcaacaggaa attcggcacg agac                44

<210> SEQ ID NO 23
<211> LENGTH: 44
<212> TYPE: DNA
<213> ORGANISM: Artificial Sequence
<220> FEATURE:
<223> OTHER INFORMATION: pint3597_Db1f

<400> SEQUENCE: 23
caacaggaaa ttcggcacga gaggacgtga accagcacct gtgc                44

<210> SEQ ID NO 24
<211> LENGTH: 34
<212> TYPE: DNA
<213> ORGANISM: Artificial Sequence
<220> FEATURE:
<223> OTHER INFORMATION: desB30f

<400> SEQUENCE: 24
ttctacacac ccaagcgcga tgttcctcag gtgg                34

```
<210> SEQ ID NO 25
<211> LENGTH: 32
<212> TYPE: DNA
<213> ORGANISM: Artificial Sequence
<220> FEATURE:
<223> OTHER INFORMATION: desB30rev

<400> SEQUENCE: 25
aggaacatcg cgcttgggtg tgtagaagaa gc                              32
```